(12) United States Patent
Grare et al.

(10) Patent No.: US 8,946,299 B2
(45) Date of Patent: Feb. 3, 2015

(54) USE OF CALIXARENES ASSOCIATED WITH AN ANTIBIOTIC IN THE TREATMENT OF BACTERIAL INFECTIONS

(75) Inventors: Marion Grare, Toulouse (FR); Raphaël Emmanuel Duval, Bioncourt (FR)

(73) Assignee: Universite de Lorraine, Nancy (FR)

( * ) Notice: Subject to any disclaimer, the term of this patent is extended or adjusted under 35 U.S.C. 154(b) by 0 days.

(21) Appl. No.: 14/110,818

(22) PCT Filed: Apr. 11, 2012

(86) PCT No.: PCT/FR2012/050789
§ 371 (c)(1),
(2), (4) Date: Nov. 19, 2013

(87) PCT Pub. No.: WO2012/140364
PCT Pub. Date: Oct. 18, 2012

(65) Prior Publication Data
US 2014/0066517 A1    Mar. 6, 2014

(30) Foreign Application Priority Data
Apr. 12, 2011 (FR) ...................................... 11 53204

(51) Int. Cl.
| | | |
|---|---|---|
| *A61K 31/04* | (2006.01) | |
| *A61K 31/155* | (2006.01) | |
| *A61K 31/427* | (2006.01) | |
| *A61K 31/43* | (2006.01) | |
| *A61K 31/496* | (2006.01) | |
| *A61K 31/546* | (2006.01) | |
| *A61K 31/57* | (2006.01) | |
| *A61K 31/665* | (2006.01) | |
| *A61K 45/06* | (2006.01) | |
| *A61K 31/4188* | (2006.01) | |
| *A61K 31/7016* | (2006.01) | |
| *A61K 31/7036* | (2006.01) | |

(52) U.S. Cl.
CPC .............. *A61K 31/155* (2013.01); *A61K 31/04* (2013.01); *A61K 31/4188* (2013.01); *A61K 31/427* (2013.01); *A61K 31/43* (2013.01); *A61K 31/496* (2013.01); *A61K 31/546* (2013.01); *A61K 31/57* (2013.01); *A61K 31/665* (2013.01); *A61K 31/7016* (2013.01); *A61K 31/7036* (2013.01); *A61K 45/06* (2013.01)
USPC ........................................... 514/634; 564/236

(58) Field of Classification Search
CPC ... A61K 31/04; A61K 31/155; A61K 31/427; A61K 31/43; A61K 31/496; A61K 31/546; A61K 31/57; A61K 31/665; A61K 45/06
See application file for complete search history.

(56) References Cited

FOREIGN PATENT DOCUMENTS

| | | |
|---|---|---|
| WO | 95/19974 | 7/1995 |
| WO | 2006/042104 | 4/2006 |

OTHER PUBLICATIONS

International Search Report PCT/FR2012/050789 dated Jun. 15, 2012.
Marion Grare et al., "In vitro activity of para-guanidinoethylcalix[4]arene against susceptible and antibiotic-resistant Gram-negative and Gram-positive bacteria", Journal of Antimicrobial Chemotherapy, vol. 60, No. 3, Sep. 2007, pp. 575-581, XP002655308.
M. Grare et al., "Cationic compounds with activity against multidrug-resistant bacteria: interest of a new compound compared with two older antiseptics, hexamidine and chlorhexidine", Clinical Microbiology and Infection: The Official Publication of the European Society of Clinical Microbiology and Infectious Diseases May 2010 Lnkd-Pubmed: 19456831, vol. 16, No. 5, May 2010, pp. 432-438, XP002655309.
M. Grare et al., "Cinetique d'action du para-guanidinoethylcalix[4]arene, et evolution de la permeabilite membranaire", Pathologie Et Biologie, L'Expansion Scientifique Francaise, Paris, FR, vol. 58, No. 1, Feb. 1, 2010, pp. 46-51, XP026894782.
Maxime Mourer et al., "Functional organisation and gain of activity: The case of the antibacterial tetra-para-guanidinoethyl-calix[4]arene", Bioorganic & Medicinal Chemistry Letters, Pergamon, Elsevier Science, GB, vol. 16, No. 11, Jun. 1, 2006, pp. 2960-2963, XP025106156.

*Primary Examiner* — Sun Jae Yoo
(74) *Attorney, Agent, or Firm* — Young & Thompson

(57) ABSTRACT

A product comprising a calixarene for its use in the treatment of pathologies involving at least one bacterial strain having a resistance to at least one defined antibiotic, on patients undergoing simultaneous or sequential treatment with a given antibiotic to which said bacterial strain optionally has a resistance.

13 Claims, 2 Drawing Sheets

USE OF CALIXARENES ASSOCIATED WITH AN ANTIBIOTIC IN THE TREATMENT OF BACTERIAL INFECTIONS

The present invention relates to the use of calixarenes in the treatment of bacterial infections.

In the field of public health, the fight against community-acquired or nosocomial bacterial infections, is always a subject of topicality and concern. In fact, bacteria are the microorganisms that are most often responsible for nosocomial infections (NI), with, in order of frequency: *Escherichia coli* (24.7%), *Staphylococcus aureus* (18.9%), *Pseudomonas aeruginosa* (10%) and *Enterococcus* spp. (6%) (RAISIN Enquiry 2006).

Certain bacteria involved in hospitals have a resistance or even a multi-resistance to the antibiotics and/or antiseptics routinely used. Multi-Resistant Bacteria are referred to as MRBs and Toto-Resistant Bacteria as TRBs. There can be mentioned for example MRSA (meticillin-resistant *Staphylococcus aureus*, with a resistance to all the β-Lactams), Enterobacteria carrying ESBL (Extended spectrum β-Lactamase) or also GRE (glycopeptide resistant *Enterococcus* spp.). Currently, 64% of the *Staphylococcus aureus* isolated during NI are meticillin-resistant (RAISIN Enquiry 2006). The problem is that the bacteria often carry several resistance mechanisms, inducing a resistance to numerous families of antibiotics: β-lactams, aminoglycosides, fluoroquinolones or macrolides etc. Moreover, this resistance to antibiotics is often associated with a resistance to the antiseptics used in the hospital environment for combating the dissemination of nosocomial infections.

The resistance of a bacterial strain to an antibiotic can be a natural resistance (characteristic of all the strains of the same species). It can be also acquired (characteristic of certain strains within a species); it then results from a modification of the gene pool of these bacteria. This type of genetic modification can confer on a bacterial strain concerned a mechanism of resistance to an antibiotic, to a family of antibiotics or to several families of antibiotics.

Fundamental research into the mechanisms used by the bacteria and the epidemiological data are currently giving rise to doubts about the possibility of eradicating these MRBs in the future. Therefore, it is no longer certain that the currently available antibiotics make it possible to control the problem over the long term. If the availability of novel antibiotics has until now made it possible to respond to each form of bacterial resistance, this approach now faces many limitations, as no new class of antibiotics has been developed for twenty five years (Boucher et al. CID, 2009). Few new antibiotics have been marketed since the start of the 90s. Among these new antibiotics, only linezolid and daptomycin have an innovative mechanism of action, but are reserved for quite specific and active applications only on Gram-positive bacteria. Moreover, they have a significant toxicity (haematological and medullar toxicity in the case of linezolid and eosinophilic pneumopathies in the case of daptomycin), which restricts their use.

However, very shortly after they were marketed, bacterial resistances appeared. Thus, by way of example, the following cases can be mentioned: linezolid, daptomycin, quinupristin-dalfopristin, or tigecycline, including in bacteria that were multi-resistant to begin with.

By using an innovative concept linking supramolecular chemistry with targeting and disorganization of the bacterial wall, a novel family of antibacterial compounds, in particular para-guanidinoethylcalix[4]arene, hereafter designated Cx1, has been developed recently. This family of compounds have antibacterial properties against different bacteria involved in nosocomial and/or community-acquired infections.

The publication by Grare et al. (J. Antimicrob. Chemother. 60 (2007), 575-581) describes that Cx1 has an antibacterial activity on bacteria which are resistant or not resistant to antibiotics.

In the publication by Grare et al. (Clin. Microbiol. Infect. 16 (2010), 432-438), the antibacterial activity of Cx1 is compared to that of hexamidine and chlorhexidine, two antiseptics which are very commonly used in human therapeutics, over a whole series of clinical isolates: MDR ("multidrug resistant"), XDR ("extended drug resistant"), even PDR ("pan-drug resistant").

The article by Grare et al. (Pathologie Biologie 58 (2010), 46-51) describes that Cx1, as a cationic antibacterial, interacts with the bacterial wall, leading in the end to a loss of membrane integrity.

Nevertheless, faced with the emergence and dissemination of numerous MRBs, it remains a matter of absolute urgency to be able to have available, novel antibacterial compounds having innovative mechanisms of action, for treating patients infected with this type of bacteria; and/or novel means making treatment with the antibiotics normally used in anti-infectious therapeutics, again accessible to these patients.

One of the aspects of the invention is to provide novel compounds making the antibiotics again accessible to patients with MRB infections.

The first aspect of the invention relates to a product comprising a calixarene represented by Formula I below:

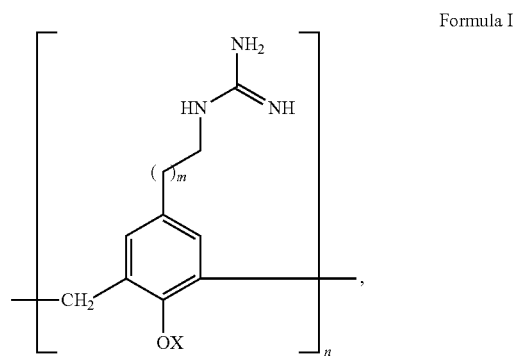

Formula I in which:
(i) n=an integer from 4 to 16,
(ii) m=an integer from 1 to 10,
(iii) X is chosen from:
a hydrogen,
an alkyl group, the number of carbons being from 1 to 20, in particular from 1 to 10,
a halogen chosen from Cl, Br, I, or
an amphiphilic group chosen from an anionic group, such as the carboxylates —$RCO_2$—, the sulphates —$RSO_4$—, the sulphonates —$RSO_3$—, a cationic group, such as $RNH_3^+$, in which R is an alkyl group, the number of carbons being from 1 to 20, in particular from 1 to 10, for its use in the treatment of pathologies involving at least one bacterial strain having a resistance to at least one "defined antibiotic", on patients undergoing simultaneous or sequential treatment with a "given antibiotic" to which said bacterial strain optionally has a resistance, or for its use in the treatment of pathologies involving a wild-type bacterial strain having no acquired resistance to any known antibiotic, on patients undergoing simultaneous or sequential treatment with a "given antibiotic" to which said bacterial strain has no resistance.

In an embodiment, the invention relates to a product comprising a calixarene represented by Formula I below:

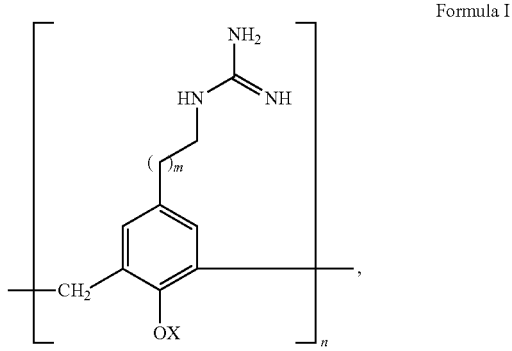

Formula I in which:
(i) n=an integer from 4 to 16,
(ii) m=an integer from 1 to 10,
(iii) X is chosen from:
a hydrogen,
an alkyl group, the number of carbons being from 1 to 20, in particular from 1 to 10,
a halogen chosen from Cl, Br, I, or
an amphiphilic group chosen from an anionic group, such as the carboxylates —$RCO_2$—, the sulphates —$RSO_4$—, the sulphonates —$RSO_3$—, a cationic group, such as $RNH_3^+$, in which R is an alkyl group, the number of carbons being from 1 to 20, in particular from 1 to 10,
for its use in the treatment of pathologies involving at least one bacterial strain having a resistance to at least one "defined antibiotic", on patients undergoing simultaneous or sequential treatment with a "given antibiotic" to which said bacterial strain optionally has a resistance.

The present invention proposes a product represented by Formula I, which makes it possible to target a specific and new category of patients who, undergoing treatment with an antibiotic designated "given antibiotic", are infected with at least one wild-type bacterial strain or bacterial strain resistant to one or more antibiotics designated "defined antibiotics".

By "a wild-type bacterial strain" is meant a bacterial strain which has no mechanisms of acquired resistance to antibiotics (only natural resistances).

By "a bacterial strain having a resistance" is meant a bacterial strain having an acquired resistance for which the MIC (Minimum Inhibitory Concentration) of the antibiotic tested is greater than the critical concentration established by EUCAST (European Committee on Antimicrobial Susceptibility Testing).

By "natural resistance" is meant a characteristic specific to all the strains of the same bacterial species. By "acquired resistance" is meant a characteristic of certain strains within the same bacterial species.

The acquired resistance can result from a modification of the gene pool making it possible for a bacterial strain to tolerate a higher antibiotic concentration than that which inhibits the susceptible strains of the same species.

Said acquired resistance can be a chromosomal resistance resulting from a mutation followed by a selection exercised by an antibiotic.

This acquired resistance can be also an extrachromosomal resistance resulting from a transfer of exogenous genetic information by plasmid, transposon or integron.

Due to the existence of this resistance, the antibiotics are administered at very high doses to the patients, or sometimes are even no longer active and can no longer be used.

The present invention is based on an unexpected fact noted by the Inventors, during evaluation of the antibacterial activity of para-guanidinoethylcalix[4]arene, hereafter designated Cx1. This molecule makes it possible to reduce the MIC of an antibiotic to which a bacterial strain has a resistance.

In other words, on the one hand, Cx1 makes it possible to confer de novo a certain level of susceptibility to (an) antibiotic(s) in a bacterial strain having an acquired resistance to said antibiotic(s), and on the other hand, Cx1 is also capable of conferring a susceptibility to (an) antibiotic(s) in a bacterial strain having a natural resistance to said antibiotic(s).

In concrete terms, in the clinical context, treatment with Cx1 in combination with at least one antibiotic makes it possible to reduce the dose of the latter in the context of the treatment of an infection with a bacterium resistant to said antibiotic, and/or to make the treatment with said antibiotic effective in patients infected with at least one bacterial strain resistant to said antibiotic.

The calixarene according to the invention can be administered to a patient simultaneously or sequentially with an antibiotic designated "given antibiotic", said patient having a pathology involving a bacterial strain having a resistance to at least one antibiotic designated "defined antibiotic".

Said strain can have a resistance to several "defined antibiotics".

Said strain may or may not have a resistance to a "given antibiotic".

By "defined antibiotic", is meant an antibiotic to which a bacterial strain is resistant.

By "given antibiotic", is meant an antibiotic utilized in a therapeutic treatment. A patient undergoing treatment with a "given antibiotic" may or may not have a resistance to this antibiotic.

Said strain can have a resistance to several "given antibiotics".

A "defined antibiotic" or a "given antibiotic" is an antibiotic known to a person skilled in the art for its antibacterial activity on certain strains of bacteria.

Said "defined antibiotic" or "given antibiotic" is different from the calixarene represented by Formula I.

By "patients undergoing simultaneous treatment ( . . . ) with a given antibiotic", is meant patients who, at least for a certain period, receive in parallel a treatment with an antibiotic designated "given antibiotic", and a treatment with a calixarene according to the invention. Moreover, the two above-mentioned treatments can be initiated or terminated one after the other.

The period of simultaneous treatment with an antibiotic and with a calixarene, determined according to the state of the patient's health, can vary between 5 days and 4 weeks.

When the patient is undergoing simultaneous treatment with an antibiotic and with a calixarene according to the invention, the administration of said standard antibiotic and that of the calixarene can be carried out at the same time or one after the other according to a fixed repetition cycle, for example one after the other over an adequate period of time.

By "patients undergoing sequential treatment with a given antibiotic", is meant patients who receive a treatment with an antibiotic before or after a treatment with a calixarene according to the invention. In other words, one of the two treatments follows the other immediately after the completion of the latter, or after an adequate rest period, for example between 1 day and one week.

In a particular embodiment, the bacterial strain infecting the patient has an acquired resistance to at least one defined antibiotic.

In a more particular embodiment, the bacterial strain infecting the patient has an acquired resistance to at least two "defined antibiotics".

These two "defined antibiotics" can belong to the same family of antibiotics or to different families.

the "given antibiotic", administered to the patient, can be an antibiotic identical to or different from a defined antibiotic, to which the bacterial strain has an acquired resistance.

The bacterial strain infecting the patient can be susceptible to the "given antibiotic", or have an acquired or natural resistance.

In a particular embodiment, the "given antibiotic" administered to the patient is different from "the defined antibiotic". The bacterial strain infecting the patient has an acquired resistance both to at least one "defined antibiotic", and to a "given antibiotic" administered to said patient.

In this case, the product of Formula I according to the invention can be used in the treatment of pathologies involving at least one bacterial strain having an acquired resistance to at least one "defined antibiotic", on patients undergoing simultaneous or sequential treatment with a given antibiotic to which said bacterial strain has an acquired resistance.

In a more particular embodiment, the bacterial strain infecting the patient has an acquired resistance both to at least two "defined antibiotics", and to a "given antibiotic" administered to said patient.

During a treatment with an antibiotic (given antibiotic) for a pathology involving a bacterial strain known for its acquired resistance to at least one other antibiotic ("defined antibiotic"), if said bacterial strain, responsible for the infection acquires a resistance to said "given antibiotic", the simultaneous or sequential administration of a calixarene according to the invention makes it possible either to restore the susceptibility of said strain to said "given antibiotic", or to reduce the dose of the "given antibiotic" administered to the patient.

In another very particular embodiment, the "given antibiotic", administered to the patient, belongs to the defined antibiotics to which the bacterial strain has a resistance.

In this case, when a patient has a pathology involving a bacterial strain known for an acquired resistance both to a "defined antibiotic" and to a "given antibiotic", the simultaneous or sequential administration of a product according to the invention and of the "given antibiotic" makes it possible either to reduce the dose of the latter administered to the patient, or to restore the susceptibility to the given antibiotic.

In another particular embodiment according to the invention, the "given antibiotic", administered to the patient, is "the defined antibiotic", to which the bacterial strain has a resistance.

In this case, the product of Formula I according to the invention can be used in the treatment of pathologies involving a bacterial strain having an acquired resistance to at least one "defined antibiotic", on patients undergoing simultaneous or sequential treatment with said antibiotic.

By way of example, if during a treatment with a given antibiotic, said strain acquires a resistance to said antibiotic, the simultaneous or sequential administration of a calixarene of Formula I according to the invention makes it possible to restore the susceptibility to said "given antibiotic".

Also by way of example, when a patient has a pathology involving a bacterial strain known for its acquired resistance to a "given antibiotic", the simultaneous or sequential treatment of the product of Formula I according to the invention and of said "given antibiotic" makes it possible either reduce the dose of the latter administered to the patient, or to restore the susceptibility of said bacterial strain to the given antibiotic.

In another particular embodiment, the bacterial strain infecting the patient is susceptible to a "given antibiotic" administered to said patient, but said strain has an acquired resistance to at least one "defined antibiotic".

In this case, the product of Formula I according to the invention can be used in the treatment of pathologies involving at least one bacterial strain having an acquired resistance to at least one "defined antibiotic", on patients undergoing simultaneous or sequential treatment with a "given antibiotic" to which said bacterial strain is susceptible.

When a patient has a pathology involving a bacterial strain known for its acquired resistance to at least one "defined antibiotic", the simultaneous or sequential administration of the product of Formula I according to the invention and of another antibiotic ("given antibiotic") to which said bacterial strain is susceptible, makes it possible to reduce the dose of said "given antibiotic" administered to the patient.

In a more particular embodiment, the bacterial strain infecting the patient which is susceptible to a "given antibiotic" administered to said patient, has an acquired resistance to at least two "defined antibiotics".

In another particular embodiment, the bacterial strain infecting the patient has a natural resistance to a "given antibiotic" administered to said patient, and an acquired resistance to at least one "defined antibiotic".

The product of Formula I according to the invention can be used in the treatment of a pathology involving at least one bacterial strain having an acquired resistance to at least one "defined antibiotic", on patients undergoing simultaneous or sequential treatment with a "given antibiotic" to which said bacterial strain has a natural resistance.

In this situation, the simultaneous or sequential administration of a product of Formula I according to the invention and of a "given antibiotic", makes it possible to confer upon said bacterial strain a susceptibility to said "given antibiotic", and as a result to reduce the dose of the "given antibiotic" administered to the patient.

In a more particular embodiment, the bacterial strain infecting the patient which has a natural resistance to a "given antibiotic" administered to said patient, has an acquired resistance to at least two "defined antibiotics".

In another embodiment, the bacterial strain infecting the patient has a natural resistance to at least one "defined antibiotic".

The "given antibiotic", administered to the patient, can be an antibiotic identical to or different from a "defined antibiotic", to which the bacterial strain has a natural resistance.

The bacterial strain infecting the patient can be susceptible to the "given antibiotic", or have an acquired or natural resistance.

In another embodiment, the bacterial strain infecting the patient has a natural resistance to at least two "defined antibiotics".

In a particular embodiment, the bacterial strain infecting the patient has a natural resistance to a "given antibiotic" administered to said patient, and to at least one "defined antibiotic" which is different from the "given antibiotic".

The product of Formula I according to the invention can be used in the treatment of pathologies involving at least one bacterial strain having a natural resistance to at least one "defined antibiotic", on patients undergoing simultaneous or sequential treatment with a "given antibiotic" to which said bacterial strain has a natural resistance.

The simultaneous or sequential administration of the product of Formula I according to the invention and of a "given antibiotic", makes it possible to confer upon said strain a susceptibility to the "given antibiotic" administered to the patient and as a result to reduce the dose of the "given antibiotic" administered to the patient.

In a more particular embodiment, the bacterial strain infecting the patient has a natural resistance to a "given antibiotic" administered to said patient, and to at least two "defined antibiotics" which are different from the given antibiotic.

In another particular embodiment, the bacterial strain infecting the patient has a natural resistance to at least one "defined antibiotic", which is identical to the "given antibiotic" administered to the patient.

The product of Formula I according to the invention can be used in the treatment of pathologies involving a bacterial strain having a natural resistance to at least one "defined antibiotic", on patients undergoing simultaneous or sequential treatment with said antibiotic.

The simultaneous or sequential administration of the product of Formula I according to the invention and of a "given antibiotic" makes it possible to confer upon said strain a susceptibility to the "given antibiotic" administered to the patient and as a result to reduce the dose of the "given antibiotic" administered to the patient.

In a more particular embodiment, the bacterial strain infecting the patient has a natural resistance to at least two "defined antibiotics", one of which is identical to the "given antibiotic" administered to the patient.

In another particular embodiment, the bacterial strain infecting the patient has a natural resistance to at least one "defined antibiotic", and is susceptible to the "given antibiotic" administered to said patient.

The product of Formula I according to the invention can be used in the treatment of pathologies involving at least one bacterial strain having a natural resistance to at least one "defined antibiotic", on patients undergoing simultaneous or sequential treatment with a "given antibiotic" to which said bacterial strain is susceptible.

The simultaneous or sequential administration of the product of Formula I according to the invention and of a "given antibiotic", makes it possible to reduce the dose of the "given antibiotic" administered to said patient.

In a particular embodiment, the bacterial strain infecting the patient has a natural resistance to at least two "defined antibiotics", and is susceptible to the "given antibiotic" administered to said patient.

In another particular embodiment, the bacterial strain infecting the patient has a natural resistance to at least one "defined antibiotic", and an acquired resistance to the "given antibiotic" administered to said patient.

The product of Formula I according to the invention can be used in the treatment of pathologies involving at least one bacterial strain having a natural resistance to at least one "defined antibiotic", on patients undergoing simultaneous or sequential treatment with a "given antibiotic" to which said bacterial strain has an acquired resistance.

The simultaneous or sequential administration of the product of Formula I according to the invention and of a "given antibiotic" makes it possible either to restore a susceptibility of said bacterial strain to the "given antibiotic", or to reduce the dose of the given antibiotic administered to the patient.

In a particular embodiment, the bacterial strain infecting the patient has a natural resistance to at least two "defined antibiotics", and an acquired resistance to the "given antibiotic" administered to said patient.

In another embodiment, the invention relates to a product comprising a calixarene represented by Formula I below:

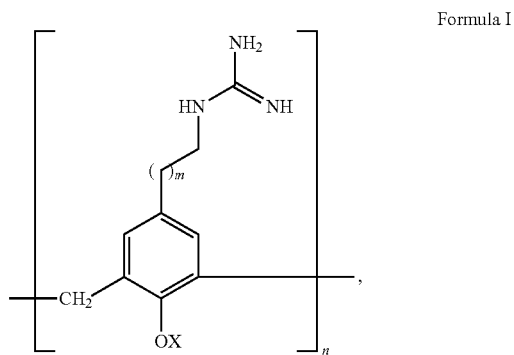

Formula I in which:
(i) n=an integer from 4 to 16,
(ii) m=an integer from 1 to 10,
(iii) X is chosen from:
a hydrogen,
an alkyl group, the number of carbons being from 1 to 20, in particular from 1 to 10,
a halogen chosen from Cl, Br, I, or
an amphiphilic group chosen from an anionic group, such as the carboxylates —$RCO_2$—, the sulphates —$RSO_4$—, the sulphonates —$RSO_3$—, a cationic group, such as $RNH_3^+$, in which R is an alkyl group, the number of carbons being from 1 to 20, in particular from 1 to 10, for its use in the treatment of pathologies involving a wild-type bacterial strain having no acquired resistance to any antibiotic, on patients undergoing simultaneous or sequential treatment with a "given antibiotic" to which said bacterial strain has no resistance.

The administration of the product of Formula I according to the invention simultaneously or sequentially with the administration of a "given antibiotic" makes it possible to reduce the dose of the "given antibiotic" administered.

According to an advantageous embodiment of the invention, the calixarene is a macrocycle (cyclic oligomer) constituted by n para-substituted or non-para-substituted phenolic units linked to each other by methylene bridges.

In an advantageous embodiment of the invention, the calixarene involved is constituted by 4 units, said calixarene corresponding to Formula I(1) below:

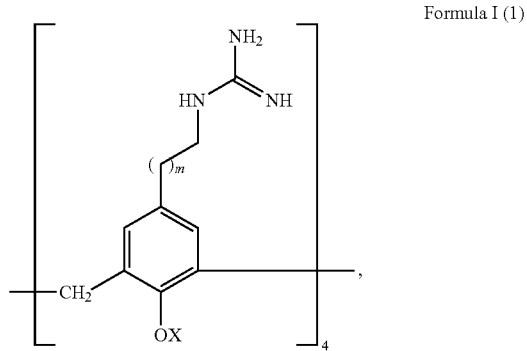

Formula I (1)

m and X having the meanings indicated above.

In another advantageous embodiment of the invention, the calixarene involved is represented by Formula I, in which m=1, said calixarene corresponding to Formula I(2) below:

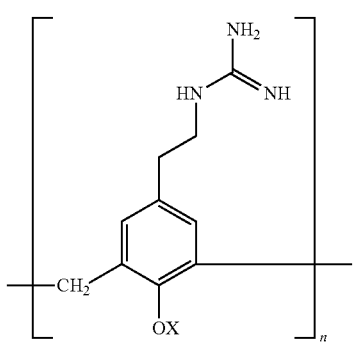

Formula I (2)

n and X having the meanings indicated above.

In another advantageous embodiment of the invention, the calixarene involved is represented by Formula I, in which X is a hydrogen, said calixarene corresponding to Formula I(3) below:

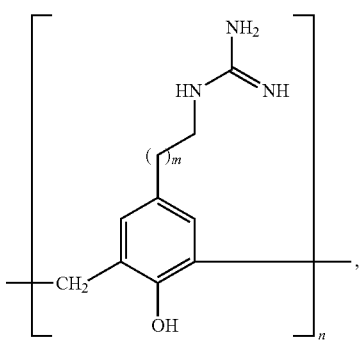

Formula I (3)

m and n having the meanings indicated above.

A particularly advantageous embodiment of the invention relates to a product for the uses described above, said product comprises a calixarene represented by Formula I, in which: n=4, m=1, X is a hydrogen, said calixarene corresponding to Formula II below:

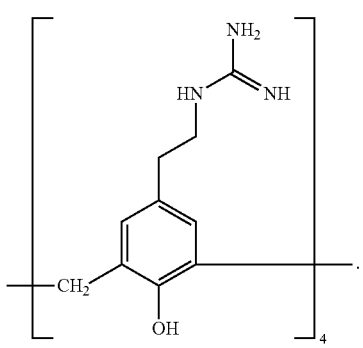

Formula II

The molecule represented by Formula II is para-guanidinoethylcalix[4]arene, designated Cx1 in the present invention.

The three-dimensional structure of the above-mentioned molecule is illustrated below.

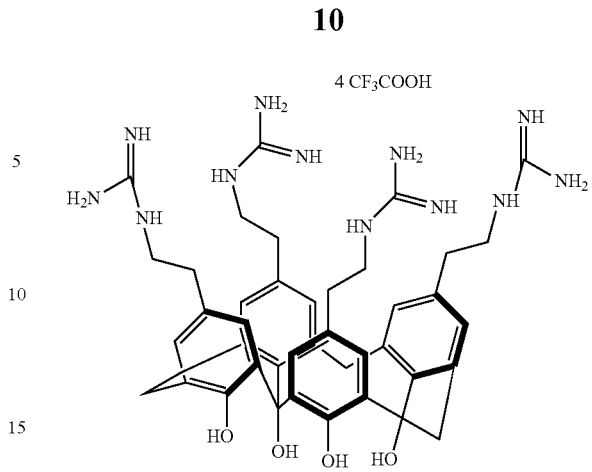

Cx1 can be synthesized according to the process described in Mourer et al. (Bioorganic & Medicinal Chemistry Letter 16 (2006) 2960-2963).

The calixarene involved in the invention can be as described above, or a salt of a physiologically acceptable acid derived from a compound of Formula (I) such as a hydrochloride, a formate, a trifluoroacetate or an oxalate (HOOC-COOH).

The expression "salt of a physiologically acceptable acid" signifies a derivative of a compound of Formula I, obtained by the reaction of an inorganic acid or an organic acid, with a compound of Formula I.

Examples of inorganic acids making it possible to obtain physiologically acceptable salts include, but are not limited to, hydrochloric acid, hydrobromic acid, nitric acid, carbonic acid, formic acid, monohydrogen carbonic acid, phosphoric acid, monohydrogen phosphoric acid, dihydrogen phosphoric acid, perchloric acid, sulphuric acid, monohydrogen sulphuric acid, hydriodic acid.

Examples of organic acids making it possible to obtain physiologically acceptable salts include, but are not limited to, acetic acid, lactic acid, propionic acid, butyric acid, isobutyric acid, palmic acid, maleic acid, glutamic acid, hydroxymaleic acid, malonic acid, benzoic acid, succinic acid, glycolic acid, suberic acid, fumaric acid, mandelic acid, phthalic acid, salicylic acid, benzenesulphonic acid, p-toluenesulphonic acid, citric acid, tartaric acid, methanesulphonic acid, hydroxynaphthoic acid.

The salts of amino acids, such as the arginates and their equivalents are also included as well as the salts of organic acids such as glucuronic acid or galacturonic acid and their equivalents (see, for example, Berge et al., "Pharmaceutical Salts", *Journal of Pharmaceutical Science*, 1977, 66, 1-19).

The calixarene involved in the invention can be used in the treatment of pathologies involving a bacterial strain having a resistance to at least one family of antibiotics, in particular in the treatment of nosocomial and/or community-acquired infections, such as abdominal infections, digestive infections, urinary infections, respiratory infections, neuro-meningeal infections, infections of the oro-pharyngeal sphere, genital infections, endocarditis, infections of the skin and soft tissues, osteoarticular infections, ocular infections, septicaemia or bacteriaemia. Table 1 below describes in more detail the infections which can be treated with a calixarene of Formula I according to the invention.

| | |
|---|---|
| abdominal infections | peritonitis, appendicitis etc. |
| digestive infections | collective food-poisoning diarrhoea, post-antibiotherapy diarrhoea etc. |
| urinary infections | cystitis, pyelonephritis, prostatitis etc. |
| respiratory infections | bronchitis, pneumonias, pneumopathies, abscess etc. |
| neuro-meningeal infections | Bacterial meningitis, cerebral abscess etc. |
| infections of the oro-pharyngeal sphere | sinusitis, otitis, anginas, phlegmons, epiglottiditis etc. |
| genital infections | vulvitis, vaginitis/vaginosis, cervicitis, salpingitis etc. |
| infections of the skin and soft tissues | furonculosis, abscess, eschar, diabetes foot etc. |
| ocular infections | conjunctivitis, keratitis, endophthalmia etc. |
| other infections | septicaemia or bacteraemia etc. |

More particularly, the calixarene involved in the invention can be used in the treatment of pathologies involving a resistant bacterial strain belonging to a species chosen from *Escherichia coli*, *Pseudomonas aeruginosa* and *Staphylococcus aureus*.

Even more particularly, the calixarene involved in the invention can be used in the treatment of the pathologies involving a strain of resistant bacteria chosen from:
a wild-type strain of *Staphylococcus aureus*
a strain of meticillin-resistant *Staphylococcus aureus* (MRSA) without associated resistance,
a strain of MRSA having a resistance to the aminoglycosides and fluoroquinolones,
a strain of MRSA having a resistance to the aminoglycosides, fluoroquinolones, macrolides-lincosamides-synergystins and ofloxacin,
a wild-type strain of *Escherichia coli*
a penicillinase-producingstrain of *Escherichia coli*, without associated resistance,
an ESBL (Extended spectrum β-Lactamase)-producing strain of *Escherichia coli* having an associated resistance to the aminoglycosides, rifampicin and the trimethoprime-sulphamethoxazole combination,
a cephalosporinase-hyperproducing strain of *Escherichia coli* having an associated resistance to the aminoglycosides, quinolones and the trimethoprime-sulphamethoxazole combination,
a wild-type strain of *Pseudomonas aeruginosa*
a strain of *Pseudomonas aeruginosa* having a resistance to the β-lactams, the trimethoprime-sulphamethoxazole combination and fosfomycin,
a strain of *Pseudomonas aeruginosa* having a resistance to the β-lactams (including the carbapenems), the aminoglycosides, the trimethoprime-sulphamethoxazole combination and ciprofloxacin,
a mucoid strain of *Pseudomonas aeruginosa* having a resistance to rifampicin and the trimethoprime-sulphamethoxazole combination.

By "a wild-type strain of *Staphylococcus aureus*", is meant a strain of *Staphylococcus aureus* which has no mechanism of acquired resistance to the antibiotics (only natural resistances).

By "a wild-type strain of *Escherichia coli*", is meant a strain of *E. coli* which has no mechanisms of acquired resistance to the antibiotics (only natural resistances).

By "a wild-type strain of *Pseudomonas aeruginosa*", is meant a strain of *P. aeruginosa* which has no mechanism of acquired resistance to the antibiotics (only natural resistances).

In a particular embodiment, the calixarene of Formula I according to the invention can be used on patients undergoing simultaneous or sequential treatment with a given antibiotic chosen from the group constituted by the β-lactams, aminoglycosides, fluoroquinolones, fosfomycin, colimycin, rifampicin, tigecycline, or fusidic acid.

The antibiotics of the family of the β-lactams include any antibiotic which contains a β-lactam ring in its molecular structure, such as amoxicillin, oxacillin, imipenem, ticarcillin, piperacillin, aztreonam, cefepime, cefotaxime, and ceftazidime.

The family of the aminoglycosides comprises, inter alia: amikacin, tobramycin, streptomycin, or gentamicin.

The family of the fluoroquinolones comprises the nalidixic acid derivatives, such as norfloxacin, ciprofloxacin, levofloxacin, or moxifloxacin.

In a more particular embodiment of the invention, the given antibiotic can be chosen from: imipenem, piperacillin-tazobactam, penicillin G, cefotaxime, ceftazidime, tobramycin, gentamicin, ciprofloxacin, rifampicin, fosfomycin, colimycin, tigecycline, ticarcilline-clavulanic acid, streptomycin or fusidic acid.

By way of example, the calixarene of Formula I according to the invention can be used on patients suffering from pathologies involving a wild-type strain of *Staphylococcus aureus*, undergoing simultaneous or sequential treatment with a given antibiotic chosen from tigecycline, fusidic acid or fosfomycin.

Also, by way of example, the calixarene of Formula I according to the invention can be used on patients suffering from pathologies involving a strain of MRSA without associated resistance, undergoing simultaneous or sequential treatment with a given antibiotic chosen from streptomycin, tigecycline, fusidic acid, or fosfomycin.

Also, by way of example, the calixarene of Formula I according to the invention can be used on patients suffering from pathologies involving a strain of MRSA having a resistance to the aminoglycosides and fluoroquinolones, undergoing simultaneous or sequential treatment with a given antibiotic chosen from penicillin G, tigecycline, fusidic acid or fosfomycin.

Also, by way of example, the calixarene of Formula I according to the invention can be used on patients suffering from pathologies involving a strain of MRSA having a resistance to the aminoglycosides, fluoroquinolones, macrolides-lincosamides-synergistins and ofloxacin, undergoing simultaneous or sequential treatment with a given antibiotic chosen from the penicillin G, the imipenem, gentamicin, tigecycline, fusidic acid or fosfomycin.

Also, by way of example, the calixarene of Formula I according to the invention can be used on patients suffering from pathologies involving a wild-type strain of *Escherichia coli*, undergoing simultaneous or sequential treatment with a given antibiotic chosen from gentamicin, tobramycin, or rifampicin.

Also, by way of example, the calixarene of Formula I according to the invention can be used on patients suffering from pathologies involving an ESBL-producing strain of *Escherichia coli*, having an associated resistance to the aminoglycosides, to rifampicin and the trimethoprime-sulphamethoxazole combination, undergoing simultaneous or sequential treatment with a given antibiotic chosen from cefotaxime, gentamicin or rifampicin.

Also, by way of example, the calixarene of Formula I according to the invention can be used on patients suffering from pathologies involving a strain of *Escherichia coli*, without associated resistance, or a cephalosporinase-hyperproducing strain of *Escherichia coli* having an associated resistance to the aminoglycosides, quinolones and the trimethoprime-sulphamethoxazole combination, undergoing simultaneous or sequential treatment with a given antibiotic chosen from gentamicin or rifampicin.

Also, by way of example, the calixarene of Formula I according to the invention can be used on patients suffering from pathologies involving a wild-type strain of *Pseudomonas aeruginosa*, undergoing simultaneous or sequential treatment with a given antibiotic chosen from piperacillin-tazobactam, ceftazidime, tobramycin, ciprofloxacin, rifampicin, fosfomycin or ticarcillin-clavulanic acid.

Also, by way of example, the calixarene of Formula I according to the invention can be used on patients suffering from pathologies involving a strain of *Pseudomonas aeruginosa* having a resistance to the β-lactams, the trimethoprime-sulphamethoxazole combination and fosfomycin, undergoing simultaneous or sequential treatment with a given antibiotic chosen from piperacillin-tazobactam, rifampicin, or tobramycin.

Also, by way of example, the calixarene of Formula I according to the invention can be used on patients suffering from pathologies involving a strain of *Pseudomonas aeruginosa* having a resistance to the β-lactams (including the carbapenems), to the aminoglycosides, the trimethoprime-sulphamethoxazole combination and ciprofloxacin, undergoing simultaneous or sequential treatment with a given antibiotic chosen from ceftazidime, rifampicin, colimycin, fosfomycin, or tobramycin.

Also, by way of example, the calixarene of Formula I according to the invention can be used on patients suffering from pathologies involving a mucoid strain of *Pseudomonas aeruginosa* having a resistance to rifampicin and the trimethoprime-sulphamethoxazole combination, undergoing simultaneous or sequential treatment with a given antibiotic chosen from the piperacillin-tazobactam, timipenem, rifampicin, colimycin, fosfomycin, tobramycin or ciprofloxacin.

The present invention also relates to a pharmaceutical composition comprising at least one product such as described above as an active substance in combination with a pharmaceutically acceptable vehicle.

Various formulations are possible for said pharmaceutical compositions: in the form of a gelatin capsule, tablet, powder, cream, lotion, aqueous or hydroalcoholic solution, mouthwash, eye drops, milk, foam, gel, spray or powder for example.

Said pharmaceutical composition can be administered by oral, parenteral, or topical route.

In such a pharmaceutical composition according to the invention, a person skilled in the art knows that the unit dose for administration of Cx1 depend of the nature of the bacteria to be treated, but also on the unit dose of a given antibiotic. The unit dose for administration of a given standard antibiotic is known to a person skilled in the art.

FIGURES

FIG. 1 represents a microplate prepared for measuring the susceptibility of a bacterial strain to a solution containing an antibiotic and Cx1 respectively in a proportion of defined concentrations. Columns 1 and 12 contain only the control medium. Columns 2 and 11 contain the control medium and bacteria, but no antibiotic or Cx1. Columns 3 to 10 contain the bacteria, Cx1 in decreasing concentration and an antibiotic in increasing concentration.

RESULTS

Figure 1:
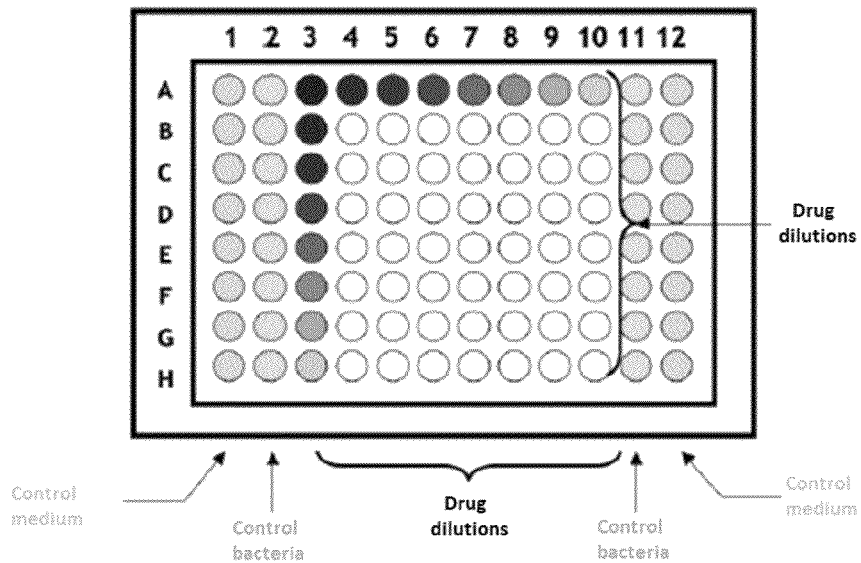

1. Equipment and Method
    1.1 Equipment and Reagent
    10, 20 or 50 mL syringe
    0.22 μm filter (Millex®GP, 0.22 μm filters, Millipore, France)
    Falcon 15 and 50 mL tubes
    96-well plates (Greiner, 650161)
    Mueller Hinton Agars (MHA) (Difco, 225250)
    Mueller Hinton Broths (MHB) (Difco, 275730)
    Sterile distilled water
    Solution of the drug to be tested: Cx1 (M=1221.11 g/mol) supplied by Prof. Regnouf de Vains in the form of white powder, taken up in sterile distilled water and filtered through a 0.22 μm filter to obtain a 10-2 mol/L sterile solution. The antibiotic was obtained commercially from the manufacturers, in the form of a ready-to-use sterile powder.
    1.2 Bacterial Strains
    Three reference strains were used, corresponding to those studied for the MICs and MBCs (Minimum Bactericidal Concentration): *Escherichia coli* ATCC 25922, *Staphylococcus aureus* ATCC 29213, *Pseudomonas aeruginosa* ATCC 27853. For each of these strains 3 corresponding clinical isolates were chosen, having various antibiotic-resistance profiles, routinely used in standard fashion:
    EcR1, EcR2, EcR3;
    SaR1, SaR3, SaR4;
    PaR2, PaR3, PaR5.
    The antibiotic susceptibility profiles of these clinical isolates are shown in the following "Identification and antibiogram" section.
    The fluctuations relative to the associated resistance type for certain strains are due to the development of the French (CA-SFM), European (EUCAST) and American (CLSI) recommendations for the categorization of the bacterial strains.
    1.3. Procedure: Chessboard Technique
    D-1: Culturing the Bacteria on MHA (Mueller Hinton Agar)
    Incubation for 24 h at 35° C.
    D0: Seeding an MHB (Mueller Hinton Broth)
    Take an "average" colony from the agar D-1 and seed 5 mL of MHB.
    Incubation for 24 h at 35° C.
    D1: Preparation of the 96-Well Plates
    Preparation of the Bacterial Inoculum:
    The purity of the strains is verified by the absence of contaminants on the MHA seeded in parallel with the broth, and by carrying out Gram staining.
    The bacterial suspension is transferred to a 15 mL Falcon tube, centrifuged for 10 min at 4500 g, then the pellet is re-suspended in 1 mL of sterile distilled water. Suitable dilutions are then prepared in order to obtain a bacterial inoculum between 5·10⁵ and 5·10⁶ CFU/mL.

Preparation of the Solutions: 1) Antibiotic (ATB) to be Tested, 2) Cx1

The MICs of the antibiotics were previously determined for each strain, by the method of microdilution in a liquid medium (CLSI (Clinical and Laboratory Standards Institute), 2003).

Suitable dilutions are prepared in order to obtain a solution having a concentration equivalent to 32 times the MIC of the ATB to be tested, in an MH (Mueller-Hinton) medium. Then a series of two-fold dilutions was prepared in MH medium in order to obtain the following concentrations: 16, 8, 4, 2, 1, 0.5 and 0.25 times the MIC (15 mL Falcon tubes). The same procedure is followed for the Cx1. This makes it possible to obtain a concentration range from 8 to 0.06 times the MIC in the microplate for the two molecules (dilution by half with addition of the 2nd molecule, then new dilution by ½ after addition of the bacterial suspension). Thus 64 ATB/Cx1 combinations are obtained.

For each plate, 1 mL of solution of each dilution is necessary.

Preparation of the Microplates

The final volume contained in each of the wells must be 100 μL. Two controls must be present on each plate:
 column 1 and 12: medium control
 column 2 and 11: medium+bacteria control
Distribution of the MH Medium
 100 μL in each of the wells of columns 1 and 12.
 50 μL in each of the wells of columns 2 and 11.
Distribution of the Dilution Range of the Antibiotic to be Tested and of the Molecule of Interest
 Cx1: 250 μL in the wells of columns 11 to 3, starting with the lowest concentration.
 ATB: 25 μL in the wells of rows H to A (columns 3 to 11), starting with the lowest concentration.
Distribution of the Bacterial Suspension
 50 μL in each of the wells of columns 2 to 11.
 D2: Reading the Turbidity at 540 Nm.

Figure 2A:
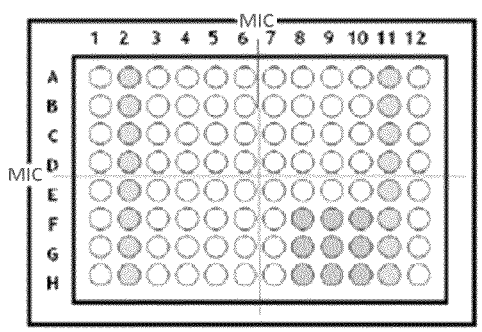
FIG. 2A shows an additivity between Cx1 and another antibiotic.
Figure 2B:
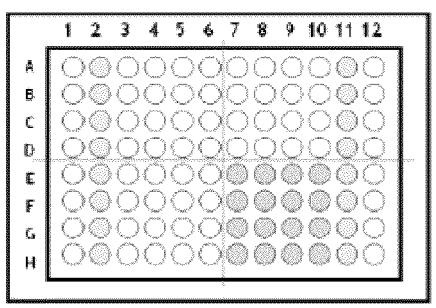
FIG. 2B shows an indifference between Cx1 and another antibiotic.
Figure 2C:
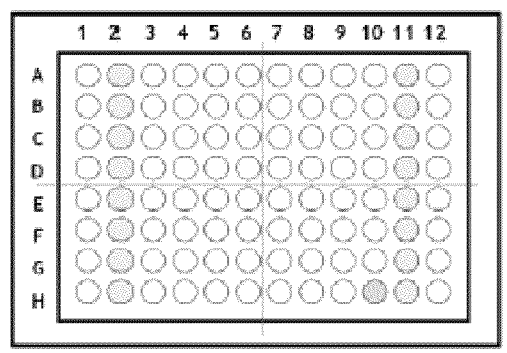
FIG. 2C shows a synergism between Cx1 and another antibiotic.
Figure 2D:
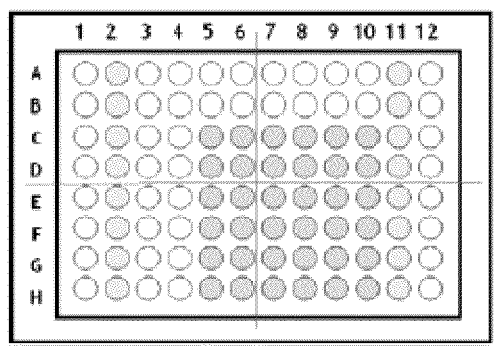
FIG. 2D shows an antagonism between Cx1 and another antibiotic.

The different types of interactions observed by the chessboard technique are shown in FIGS. 2A, 2B, 2C and 2D:

The FIC (Fractional Inhibitory Concentration Index) value is determined by the following formula:

$$FIC = FIC_A + FIC_B = \frac{MIC_A \text{ in comb.}}{MIC_A \text{ alone}} + \frac{MIC_B \text{ in comb.}}{MIC_B \text{ alone}}$$

$MIC_A$ in combination $MIC_A$ alone $MIC_B$ in combination $MIC_B$ alone

When $FIC \leq 0.5$, there is a synergistic effect between antibiotic A and antibiotic B.

When $0.5 < FIC \leq 1$, there is an additive effect between antibiotic A and antibiotic B.

When $1 < FIC \leq 4$, there is an indifferent effect between antibiotic A and antibiotic B.

When $FIC > 4$, there is an antagonistic effect between antibiotic A and antibiotic B.

For each strain and each antibiotic/Cx1 combination, the experiments were repeated a minimum of 3 times.

2. Results & Discussion

The results obtained are presented in the form of tables (Tables I to XII), showing in greater detail and by ATB/Cx1 pair: the MICs of the compounds used alone (initial MICs);
 the ranges tested;
 the FIC indices obtained during the different experiments;
 the optimum concentrations for the synergism;
 the Cx1 dilution factor corresponding to the difference in dosage existing between the use of Cx1 alone or in combination with an antibiotic;
 the dilution factor of the antibiotic corresponding to the difference in dosage existing between the use of the antibiotic alone or in combination with Cx1;
 the nature of the interaction observed.

The results below show that no antagonism was observed between Cx1 and an antibiotic tested, irrespective of the strains and combinations tested.

The results also demonstrate that the treatment with Cx1 in combination with the treatment with an antibiotic for a pathology involving a bacterial strain resistant to said antibiotic makes it possible:
 to confer upon the bacterial strain a certain level of susceptibility to said antibiotic;
 to reduce the dose of said antibiotic as well as the dose of Cx1 administered.

The results demonstrate that the treatment with Cx1 in combination with the treatment with a given antibiotic for a pathology involving a bacterial strain having a resistance to a specific antibiotic makes it possible to reduce the dose of given antibiotic as well as the dose of Cx1 administered.

These results are equally valid for the treatment with Cx1 in combination with the treatment with a given antibiotic for a pathology involving a bacterial strain having a resistance to at least two different families of antibiotics. This is the case with the tested strains SaR3, EcR2, SaR4, PaR2 and PaR3.

Among all of the strains analyzed, *Pseudomonas aeruginosa* is the strain for which the greatest number of synergistic combinations with very varied antibiotics (β-lactams, aminoglycosides, fluoroquinolones, etc.), was observed.

Moreover, the antibiotics for which a synergism between same and Cx1 was observed, act at the level of:
 the wall: fosfomycin (in the knowledge that the specific mechanism of action of fosfomycin is demonstrated by quasi-constant synergistic activity with the other antibiotics active on the bacterial wall) but also with the piperacillin-tazobactam & ticarcillin-clavulanic acid combinations, and ceftazidime;
 protein synthesis: tigecycline, gentamicin, tobramycin, streptomycin, fusidic acid;
 nucleic acid synthesis: rifampicin, ciprofloxacin.

2. Synergism of the Combination of Cx1 with Antibiotics Against *Escherichia coli* Strains, Antibiotic-Resistant or not 2.1.

TABLE I

Synergism against the *Escherichia coli* strain ATCC 25922 (wild type) (n = 4)

| Combinations | Initial MICs (mg/L) | Ranges tested (mg/L) | FIC index | Optimum MICs (mg/L) | Difference Cx1 MIC | Difference ATB MIC | Finding |
|---|---|---|---|---|---|---|---|
| Cx1/Amoxicillin | 4/4 | 32/32 | 1-4 | nd | nd | Nd | Indifference |
| Cx1/Amoxicillin-clavulanic acid | 4/4 | 16/256 | 0.53-1 | 0.125/2 | ↓ x5 | ↓ x1 | Additivity |

TABLE I-continued

Synergism against the *Escherichia coli* strain ATCC 25922 (wild type) (n = 4)

| Combinations | Initial MICs (mg/L) | Ranges tested (mg/L) | FIC index | Optimum MICs (mg/L) | Difference Cx1 MIC | Difference ATB MIC | Finding |
|---|---|---|---|---|---|---|---|
| Cx1/Piperacillin | 4/2 | 16/256 | 1-4 | nd | nd | nd | Indifference |
| Cx1/Cefotaxime | 4/0.06 | 16/1 | 0.53-1 | 0.125/0.03 | ↓ x5 | ↓ x1 | Additivity |
| Cx1/Ceftazidime | 4/0.125 | 16/1 | 0.62-0.98 | 2/0.015 | ↓ x1 | ↓ x3 | Additivity |
| Cx1/Imipenem | 4/0.125 | 16/1 | 1-4 | nd | nd | nd | Indifference |
| Cx1/Ertapenem | 4/0.015 | 16/1 | 0.625-1 | 1/0.07 | ↓ x2 | ↓ x1 | Additivity |
| Cx1/Gentamicin | 4/0.125 | 16/4 | 0.27-0.98 | 0.125/0.03 | ↓ x5 | ↓ x2 | Synergism |
| Cx1/Amikacin | 4/0.25 | 16/4 | 1-4 | nd | nd | nd | Indifference |
| Cx1/Tobramycin | 4/0.25 | 16/4 | 0.365-1 | 0.5/0.06 | ↓ x3 | ↓ x2 | Synergism |
| Cx1/Ciprofloxacin | 2/0.015 | 16/1 | 1-4 | nd | nd | nd | Indifference |
| Cx1/Rifampicin | 4/4 | 16/16 | 0.16-1 | 0.5/0.125 | ↓ x3 | ↓ x5 | Synergism |

2.2.

TABLE II

Synergism against a penicillinase-producing strain of *Escherichia coli* without associated resistance (or EcR1) (n = 4)

| Combinations | Initial MICs (mg/L) | Ranges tested (mg/L) | FIC index | Optimum concentrations (mg/L) | Difference Cx1 MIC | Difference ATB MIC | Finding |
|---|---|---|---|---|---|---|---|
| Cx1/Amoxicillin | 2/>256 | 32/256 | 1-4 | nd | nd | nd | Indifference |
| Cx1/Amoxicillin-clavulanic acid | 2/16 | 16/256 | 1-4 | nd | nd | nd | Indifference |
| Cx1/Piperacillin | 2/256 | 16/256 | 1-4 | nd | nd | nd | Indifference |
| Cx1/Cefotaxime | 2/0.06 | 16/1 | 0.75-1 | 1/0.015 | ↓ x1 | ↓ x2 | Additivity |
| Cx1/Ceftazidime | 2/0.25 | 16/1 | 0.56-1 | 0.125/0.125 | ↓ x4 | ↓ x1 | Additivity |
| Cx1/Imipenem | 2/0.125 | 16/1 | 1-4 | nd | nd | nd | Indifference |
| Cx1/Ertapenem | 2/0.015 | 16/1 | 0.75-1 | 0.5/0.07 | ↓ x2 | ↓ x1 | Additivity |
| Cx1/Gentamicin | 2/0.125 | 16/4 | 0.3-1 | 0.125/0.03 | ↓ x4 | ↓ x2 | Synergism |
| Cx1/Amikacin | 2/0.25 | 16/4 | 1-4 | nd | nd | nd | Indifference |
| Cx1/Tobramycin | 2/0.25 | 16/4 | 1-4 | nd | nd | nd | Indifference |
| Cx1/Ciprofloxacin | 2/0.015 | 16/1 | 1-4 | nd | nd | nd | Indifference |
| Cx1/Rifampicin | 2/4 | 16/16 | 0.28-1 | 0.5/0.125 | ↓ x2 | ↓ x5 | Synergism |

2.3.

TABLE III

Synergism against an ESBL-producing strain of *Escherichia coli*, having an associated resistance to the aminoglycosides, rifampicin and the trimethoprim-sulphamethoxazole combination (or EcR3) (n = 4)

| Combinations | Initial MICs (mg/L) | Ranges tested (mg/L) | FIC index | Optimum concentrations (mg/L) | Difference Cx1 MIC | Difference ATB MIC | Finding |
|---|---|---|---|---|---|---|---|
| Cx1/Amoxicillin | 2/>256 | 16/256 | 1-4 | nd | nd | nd | Indifference |
| Cx1/Amoxicillin-clavulanic acid | 2/32 | 16/256 | 0.56-1 | 0.125/16 | ↓ x4 | ↓ x1 | Additivity |
| Cx1/Piperacillin | 2/128 | 16/256 | 1-4 | nd | nd | nd | Indifference |
| Cx1/Cefotaxime | 2/128 | 16/256 | 0.375-1 | 0.25/32 | ↓ x3 | ↓ x2 | Synergism |
| Cx1/Ceftazidime | 2/1 | 16/16 | 0.56-1 | 0.125/0.5 | ↓ x4 | ↓ x1 | Additivity |
| Cx1/Imipenem | 2/0.125 | 16/1 | 1-4 | nd | nd | nd | Indifference |
| Cx1/Ertapenem | 2/0.0015 | 16/1 | 1-4 | nd | nd | nd | Indifference |
| Cx1/Gentamicin | 2/2 | 16/4 | 0.31-1 | 0.125/0.5 | ↓ x4 | ↓ x3 | Synergism |
| Cx1/Amikacin | 2/1 | 16/4 | 1-4 | nd | nd | nd | Indifference |
| Cx1/Tobramycin | 2/4 | 16/4 | 1-4 | nd | nd | nd | Indifference |
| Cx1/Ciprofloxacin | 2/0.06 | 16/1 | 0.56-1 | 0.125/0.03 | ↓ x4 | ↓ x1 | Additivity |
| Cx1/Rifampicin | 2/4 | 16/16 | 0.25-1 | 0.25/0.5 | ↓ x3 | ↓ x3 | Synergism |

2.4.

TABLE IV

Synergism against a cephalosporinase-hyperproducing strain of *Escherichia coli* having an associated resistance to aminoglycosides, quinolones and the trimethoprim-sulphamethoxazole combination (or EcR2) (n = 4)

| Combinations | Initial MICs (mg/L) | Ranges tested (mg/L) | FIC index | Optimum concentrations (mg/L) | Difference Cx1 MIC | Difference ATB MIC | Finding |
|---|---|---|---|---|---|---|---|
| Cx1/Amoxicillin | 2/256 | 16/256 | 1-4 | nd | nd | nd | Indifference |
| Cx1/Amoxicillin-clavulanic acid | 2/256 | 32/256 | 0.56-1 | 0.125/128 | ↓ x4 | ↓ x1 | Additivity |
| Cx1/Piperacillin | 2/32 | 16/256 | 0.56-1 | 0.125/16 | ↓ x4 | ↓ x1 | Additivity |
| Cx1/Cefotaxime | 2/4 | 16/32 | 1-4 | nd | nd | nd | Indifference |
| Cx1/Ceftazidime | 2/8 | 16/32 | 1-4 | nd | nd | nd | Indifference |
| Cx1/Imipenem | 2/0.125 | 16/1 | 1-4 | nd | nd | nd | Indifference |
| Cx1/Ertapenem | 2/0.03 | 16/1 | 1-4 | nd | nd | nd | Indifference |
| Cx1/Gentamicin | 2/2 | 16/4 | 0.31-1 | 0.125/0.5 | ↓ x4 | ↓ x2 | Synergism |
| Cx1/Amikacin | 2/0.5 | 16/4 | 1-4 | nd | nd | nd | Indifference |
| Cx1/Tobramycin | 2/4 | 16/4 | 1-4 | nd | nd | nd | Indifference |
| Cx1/Ciprofloxacin | 2/0.015 | 16/1 | 1-4 | nd | nd | nd | Indifference |
| Cx1/Rifampicin | 2/2 | 16/16 | 0.31-1 | 0.25/0.5 | ↓ x3 | ↓ x2 | Synergism |

3. Synergism of the Combination of Cx1 with Antibiotics Against *Staphylococcus aureus* Strains, Antibiotic-Resistant or not 3.1.

TABLE V

Synergism against the *Staphylococcus aureus* strain ATCC 29213 (wild type) (n = 4)

| Combinations | Initials MIC (mg/L) | Ranges tested (mg/L) | FIC index | Optimum concentrations (mg/L) | Difference Cx1 MIC | Difference ATB MIC | Finding |
|---|---|---|---|---|---|---|---|
| Cx1/Penicillin G | 8/1 | 64/4 | 0.5-1 | 2/0.25 | ↓ x2 | ↓ x2 | Additivity |
| Cx1/Imipenem | 8/0.015 | 64/1 | 1-4 | nd | nd | nd | Indifference |
| Cx1/Erythromycin | 8/0.5 | 64/4 | 1-4 | nd | nd | nd | Indifference |
| Cx1/Vancomycin | 8/0.5 | 64/4 | 0.75-1 | 4/0.125 | ↓ x1 | ↓ x2 | Additivity |
| Cx1/Levofloxacin | 8/0.125 | 64/4 | 1-4 | nd | nd | nd | Indifference |
| Cx1/Amikacin | 8/1 | 64/4 | 0.53-1 | 4/0.03 | ↓ x1 | ↓ x5 | Additivity |
| Cx1/Gentamicin | 8/0.25 | 64/2 | 0.49-1 | 2/0.06 | ↓ x2 | ↓ x2 | Additivity |
| Cx1/Streptomycin | 8/4 | 64/32 | 0.375-1 | 1/1 | ↓ x3 | ↓ x2 | Synergism |
| Cx1/Linezolid | 8/2 | 64/8 | 1-4 | nd | nd | nd | Indifference |
| Cx1/Tigecycline | 8/0.25 | 64/2 | 0.18-1 | 0.5/0.03 | ↓ x4 | ↓ x3 | Synergism |
| Cx1/Fusidic acid | 8/2 | 64/8 | 0.125-1 | 0.5/0.125 | ↓ x4 | ↓ x4 | Synergism |
| Cx1/Fosfomycin | 8/8 | 64/32 | 0.18-1 | 0.5/1 | ↓ x4 | ↓ x3 | Synergism |

3.2.

TABLE VI

Synergism against an MRSA strain without associated resistance (or SaR1) (n = 4)

| Combinations | MIC (mg/L) | Ranges tested (mg/L) | FIC index | Optimum concentrations (mg/L) | Difference Cx1 MIC | Difference ATB MIC | Finding |
|---|---|---|---|---|---|---|---|
| Cx1/Penicillin G | 8/0.5 | 64/4 | 0.5-1 | 2/0.125 | ↓ x2 | ↓ x2 | Additivity |
| Cx1/Imipenem | 8/0.25 | 64/4 | 0.625-1 | 0.5/0.06 | ↓ x4 | ↓ x2 | Additivity |
| Cx1/Erythromycin | 8/0.5 | 64/4 | 1-4 | nd | nd | nd | Indifference |
| Cx1/Vancomycin | 8/0.25 | 64/4 | 1-4 | nd | nd | nd | Indifference |
| Cx1/Levofloxacin | 8/0.25 | 64/4 | 1-4 | nd | nd | nd | Indifference |
| Cx1/Gentamicin | 8/0.25 | 64/2 | 0.49-1 | 2/0.06 | ↓ x2 | ↓ x2 | Additivity |
| Cx1/Streptomycin | 8/4 | 64/32 | 0.75-1 | 4/1 | ↓ x1 | ↓ x2 | Additivity |
| Cx1/Linezolid | 8/2 | 64/8 | 1-4 | nd | nd | nd | Indifference |
| Cx1/Tigecycline | 8/0.25 | 64/2 | 0.18-1 | 0.5/0.03 | ↓ x4 | ↓ x3 | Synergism |
| Cx1/Fusidic acid | 8/0.5 | 64/8 | 0.245-1 | 1/0.06 | ↓ x3 | ↓ x3 | Synergism |
| Cx1/Fosfomycin | 8/2 | 64/32 | 0.31-1 | 0.5/0.5 | ↓ x4 | ↓ x2 | Synergism |

3.3.

TABLE VII

Synergism against an MRSA strain having a resistance to the aminoglycosides and fluoroquinolones (SaR3) (n = 4)

| Combinations | MIC (mg/L) | Ranges tested (mg/L) | FIC index | Optimum concentrations (mg/L) | Difference Cx1 MIC | Difference ATB MIC | Finding |
|---|---|---|---|---|---|---|---|
| Cx1/Penicillin G | 8/0.5 | 64/4 | 0.375-1 | 2/0.06 | ↓ x2 | ↓ x3 | Synergism |
| Cx1/Imipenem | 8/0.25 | 64/4 | 0.56-1 | 2/0.06 | ↓ x2 | ↓ x2 | Additivity |
| Cx1/Erythromycin | 8/0.5 | 64/4 | 1-4 | nd | nd | nd | Indifference |
| Cx1/Vancomycin | 8/0.25 | 64/4 | 1-4 | nd | nd | nd | Indifference |
| Cx1/Levofloxacin | 8/8 | 64/32 | 1-4 | nd | nd | nd | Indifference |
| Cx1/Gentamicin | 8/0.125 | 64/2 | 0.74-1 | 4/0.03 | ↓ x1 | ↓ x2 | Additivity |
| Cx1/Streptomycin | 8/4 | 64/32 | 0.625-1 | 1/2 | ↓ x3 | ↓ x1 | Additivity |
| Cx1/Linezolid | 8/2 | 64/8 | 1-4 | nd | nd | nd | Indifference |
| Cx1/Tigecycline | 8/0.25 | 64/2 | 0.245-1 | 1/0.03 | ↓ x3 | ↓ x3 | Synergism |
| Cx1/Fusidic acid | 8/0.25 | 64/8 | 0.365-1 | 1/0.06 | ↓ x3 | ↓ x2 | Synergism |
| Cx1/Fosfomycin | 8/16 | 64/32 | 0.18-1 | 0.5/2 | ↓ x4 | ↓ x3 | Synergism |

3.4.

TABLE VIII

Synergism against an MRSA strain having a resistance to the aminoglycosides, fluoroquinolones, macrolides-lincosamides-synergistins and ofloxacin (SaR4) (n = 4)

| Combinations | MIC (mg/L) | Ranges tested (mg/L) | FIC index | Optimum concentrations (mg/L) | Difference Cx1 MIC | Difference ATB MIC | Finding |
|---|---|---|---|---|---|---|---|
| Cx1/Penicillin G | 8/4 | 64/32 | 0.375-1 | 2/0.5 | ↓ x2 | ↓ x3 | Synergism |
| Cx1/Imipenem | 8/2 | 64/32 | 0.375-1 | 1/0.5 | ↓ x3 | ↓ x2 | Synergism |
|  |  |  |  | 2/0.25 | ↓ x2 | ↓ x3 |  |
| Cx1/Erythromycin | 8/>32 | 64/32 | 1-4 | nd | nd | nd | Indifference |
| Cx1/Vancomycin | 8/0.25 | 64/4 | 1-4 | nd | nd | nd | Indifference |
| Cx1/Levofloxacin | 8/>32 | 64/32 | 1-4 | nd | nd | nd | Indifference |
| Cx1/Gentamicin | 8/0.25 | 64/2 | 0.30-1 | 0.5/0.06 | ↓ x4 | ↓ x2 | Synergism |
| Cx1/Streptomycin | 8/4 | 64/32 | 0.625-1 | 4/0.5 | ↓ x1 | ↓ x3 | Additivity |
| Cx1/Linezolid | 8/2 | 64/8 | 0.56-1 | 0.5/1 | ↓ x4 | ↓ x1 | Additivity |
| Cx1/Tigecycline | 8/0.25 | 64/2 | 0.18-1 | 0.5/0.03 | ↓ x4 | ↓ x3 | Synergism |
| Cx1/Fusidic acid | 8/4 | 64/8 | 0.08-1 | 0.5/0.06 | ↓ x4 | ↓ x6 | Synergism |
| Cx1/Fosfomycin | 8/128 | 64/32 | 1-4 | nd | nd | nd | Indifference |

4. Synergism of the Combination of Cx1 with Antibiotics Against *Pseudomonas aeruginosa* Strains, Antibiotic-Resistant or not 4.1.

TABLE IX

Synergism against the *Pseudomonas aeruginosa* strain ATCC 27853 (wild type) (n = 4)

| Combinations | MIC (mg/L) | Ranges tested (mg/L) | FIC index | Optimum concentrations (mg/L) | Difference Cx1 MIC | Difference ATB MIC | Finding |
|---|---|---|---|---|---|---|---|
| Cx1/Ticarcillin-clavulanic acid | 32/8 | 256/32 | 0.375-1 | 4/1 | ↓ x3 | ↓ x3 | Synergism |
| Cx1/Piperacillin-Tazobactam | 32/16 | 256/128 | 0.31-1 | 2/4 | ↓ x4 | ↓ x2 | Synergism |
| Cx1/Ceftazidime | 32/4 | 256/64 | 0.375-1 | 4/1 | ↓ x3 | ↓ x2 | Synergism |
| Cx1/Imipenem | 32/2 | 256/16 | 0.5-4 | 8/0.5 | ↓ x2 | ↓ x2 | Additivity |
| Cx1/Rifampicin | 32/64 | 256/256 | 0.12-1 | 2/4 | ↓ x4 | ↓ x4 | Synergism |
| Cx1/Colimycin | 32/4 | 256/64 | 0.5-1 | nd | nd | nd | Additivity |
| Cx1/Fosfomycin | 32/16 | 256/256 | 0.375-1 | 4/4 | ↓ x3 | ↓ x2 | Synergism |
|  |  |  |  | 2/8 | ↓ x4 | ↓ x1 |  |
| Cx1/Tobramycin | 32/0.5 | 256/4 | 0.18-1 | 2/0.06 | ↓ x4 | ↓ x3 | Synergism |
| Cx1/Amikacin | 32/0.5 | 256/4 | 1-4 | nd | nd | nd | Indifference |
| Cx1/Ciprofloxacin | 32/0.5 | 256/4 | 0.185-1 | 4/0.125 | ↓ x3 | ↓ x2 | Synergism |

4.2.

TABLE X

Synergism against a *Pseudomonas aeruginosa* strain having a resistance to β-lactams, the trimethoprim-sulphamethoxazole combination and fosfomycin (or PaR2) (n = 4)

| Combinations | MIC (mg/L) | Ranges tested (mg/L) | FIC index | Optimum concentrations (mg/L) | Difference Cx1 MIC | Difference ATB MIC | Finding |
|---|---|---|---|---|---|---|---|
| Cx1/Ticarcillin-Clavulanic acid | 32/512 | 256/512 | 1-4 | nd | nd | nd | Indifference |
| Cx1/Piperacillin-Tazobactam | 32/512 | 256/512 | 0.25-1 | 4/64 | ↓ x3 | ↓ x3 | Synergism |
| Cx1/Ceftazidime | 32/8 | 256/64 | 1-4 | nd | nd | nd | Indifference |
| Cx1/Imipenem | 32/2 | 256/16 | 0.5-4 | 8/1 | ↓ x2 | ↓ x1 | Additivity |
| Cx1/Rifampicin | 32/64 | 256/256 | 0.185-1 | 4/4 | ↓ x3 | ↓ x4 | Synergism |
| | | | | 8/2 | ↓ x2 | ↓ x5 | |
| Cx1/Colimycin | 32/8 | 256/64 | 1-4 | nd | nd | nd | Indifference |
| Cx1/Fosfomycin | 32/64 | 256/256 | 0.5-4 | 16/32 | ↓ x1 | ↓ x1 | Additivity |
| Cx1/Tobramycin | 32/1 | 256/4 | 0.31-1 | 2/0.25 | ↓ x4 | ↓ x2 | Synergism |
| Cx1/Amikacin | 32/1 | 256/4 | 1-4 | nd | nd | nd | Indifference |
| Cx1/Ciprofloxacin | 32/1 | 256/4 | 0.5-4 | nd | nd | nd | Additivity |

4.3.

TABLE XI

Synergism against a *Pseudomonas aeruginosa* strain having a resistance to β-lactams (including the carbapenems), aminoglycosides, the trimethoprim-sulphamethoxazole combination and ciprofloxacin (or PaR3) (n = 4)

| Combinations | MIC (mg/L) | Ranges tested (mg/L) | FIC index | Optimum concentrations (mg/L) | Difference Cx1 MIC | Difference ATB MIC | Finding |
|---|---|---|---|---|---|---|---|
| Cx1/Ticarcillin-Clavulanic acid | 32/512 | 256/512 | 1-4 | nd | nd | nd | Indifference |
| Cx1/Piperacillin-Tazobactam | 32/512 | 256/512 | 1-4 | nd | nd | nd | Indifference |
| Cx1/Ceftazidime | 32/16 | 256/64 | 0.31-1 | 2/4 | ↓ x4 | ↓ x2 | Synergism |
| Cx1/Imipenem | 32/32 | 256/256 | 0.5-1 | 8/8 | ↓ x2 | ↓ x2 | Additivity |
| Cx1/Rifampicin | 32/32 | 256/256 | 0.09-1 | 2/2 | ↓ x4 | ↓ x4 | Synergism |
| Cx1/Colimycin | 32/8 | 256/64 | 0.155-1 | 4/0.5 | ↓ x3 | ↓ x4 | Synergism |
| Cx1/Fosfomycin | 32/>64 | 256/256 | 0.31-1 | 2/64 | ↓ x4 | >↓ x2 | Synergism |
| Cx1/Tobramycin | 32/64 | 256/256 | 0.185-1 | 2/8 | ↓ x4 | ↓ x3 | Synergism |
| Cx1/Amikacin | 32/1 | 256/4 | 1-4 | nd | nd | nd | Indifference |
| Cx1/Ciprofloxacin | 32/0.5 | 256/4 | 0.5/4 | 8/0.125 | ↓ x2 | ↓ x2 | Additivity |

4.4.

TABLE XII

Synergism against a mucoid strain of *Pseudomonas aeruginosa* having a resistance to rifampicin and the trimethoprim-sulphamethoxazole combination (or PaR5) (n = 4)

| Combinations | MIC (mg/L) | Ranges tested (mg/L) | FIC index | Optimum concentrations (mg/L) | Difference Cx1 MIC | Difference ATB MIC | Finding |
|---|---|---|---|---|---|---|---|
| Cx1/Ticarcillin-Clavulanic acid | 32/32 | 256/512 | 1-4 | nd | nd | nd | Indifference |
| Cx1/Piperacillin-Tazobactam | 32/32 | 256/512 | 0.31-1 | 2/8 | ↓ x4 | ↓ x2 | Synergism |
| Cx1/Ceftazidime | 32/8 | 256/64 | 1-4 | nd | nd | nd | Indifference |
| Cx1/Imipenem | 32/2 | 256/16 | 0.25-1 | 4/0.25 | ↓ x3 | ↓ x3 | Synergism |
| Cx1/Rifampicin | 32/16 | 256/256 | 0.185-1 | 2/2 | ↓ x4 | ↓ x3 | Synergism |
| Cx1/Colimycin | 32/16 | 256/64 | 0.187-1 | 2/2 | ↓ x4 | ↓ x3 | Synergism |
| Cx1/Fosfomycin | 32/16 | 256/256 | 0.375-1 | 8/2 | ↓ x2 | ↓ x3 | Synergism |
| | | | | 4/4 | ↓ x3 | ↓ x2 | |
| Cx1/Tobramycin | 32/1 | 256/4 | 0.25-1 | 4/0.125 | ↓ x3 | ↓ x3 | Synergism |
| Cx1/Amikacin | 32/0.5 | 256/4 | 1-4 | nd | nd | nd | Indifference |
| Cx1/Ciprofloxacin | 32/1 | 256/4 | 0.31-1 | 2/0.25 | ↓ x4 | ↓ x2 | Synergism |

5. Identification and Antibiogram
5.1 EcR1: Penicillinase-Producing *Escherichia coli* without Associated Resistance The bacterial and antibiogram identification is carried out by the VITEK 2 system (bioMérieux) and by the disk diffusion technique.

TABLE A1

| Antibiotics | Diameter | Dmin Dmax | Results | MIC mg/L | Results |
|---|---|---|---|---|---|
| Amoxicillin | 6 | 14-21 | Resistant | ≥32 | Resistant |
| Amox + clavulanic acid | 20 | 14-21 | Intermediate | 4 | Susceptible |
| Ticarcillin | 6 | 18-22 | Resistant | ≥128 | Resistant |
| Piperacillin | 17 | 12-20 | Intermediate | ≤8 | Susceptible |
| Piper + tazobactam | 25 | 14-21 | Susceptible | ≤4 | Susceptible |
| C1G | 17 | 12-18 | Intermediate | 4 | Susceptible |
| Cefoxitin | 24 | 15-22 | Susceptible | ≤4 | Susceptible |
| Cefotaxime | 30 | 15-21 | Susceptible | ≤1 | Susceptible |
| Ceftazidime | | | | ≤1 | Susceptible |
| Imipenem | | | | ≤1 | Susceptible |
| Aztreonam | 28 | 17-23 | Susceptible | | |
| Tobramycin | 19 | 14-16 | Susceptible | ≤1 | Susceptible |
| Gentamicin | 20 | 14-16 | Susceptible | ≤1 | Susceptible |
| Amikacin | 19 | 15-17 | Susceptible | ≤2 | Susceptible |
| Netilmicin | 24 | 17-19 | Susceptible | ≤1 | Susceptible |
| Minocycline | 20 | 17-19 | Susceptible | | |
| Colistin | 15 | 15 | Susceptible | | |
| Trimethoprim-Sulphamet. | 21 | 10-16 | Susceptible | ≤20 | Susceptible |
| Nalidixic acid | | | | ≤2 | Susceptible |
| Norfloxacin | | | | ≤0.5 | Susceptible |
| Ofloxacin | | | | ≤0.25 | Susceptible |
| Pefloxacin | 26 | 16-22 | Susceptible | | |
| Ciprofloxacin | 27 | 19-22 | Susceptible | ≤0.25 | Susceptible |
| Rifampicin | 16 | 14-19 | Intermediate | | |
| Fosfomycin | 24 | 14 | Susceptible | | |
| Nitrofurantoin | | | | ≤16 | Susceptible |
| Cefepime | 27 | 15-21 | Susceptible | | |

TABLE A2

| Antibiotics | MIC mg/L (diameter in mm) | Cc CA-SFM 2011 mg/L | CA-SFM Interpretation | Cc EUCAST 2011 | EUCAST Interpretation | Cc CLSI 2011 | CLSI Interpretation |
|---|---|---|---|---|---|---|---|
| Amoxicillin | ≥32 | 4-8 | Resistant | 8 | Resistant | 8-32 | Resistant |
| Amox + Clavulanic acid | 4 | 4-8 | Susceptible | 8 | Susceptible | 8-32 | Susceptible |
| Ticarcillin | ≥128 | 8-16 | Resistant | 8-16 | Resistant | 16-128 | Resistant |
| Piperacillin | ≤8 | 8-16 | Susceptible | 8-16 | Susceptible | 16-128 | Susceptible |
| Piper + tazobactam | ≤4 | 8-16 | Susceptible | 8-16 | Susceptible | 16-128 | Susceptible |
| Cefalotine | 4 | 8-32 | Susceptible | 16 | Susceptible | 8-32 | Susceptible |
| Cefoxitin | ≤4 | 8-32 | Susceptible | NA | — | 8-32 | Susceptible |
| Cefotaxime | ≤1 | 1-2 | Susceptible | 1-2 | Susceptible | 1-4 | Susceptible |
| Ceftazidime | ≤1 | 1-4 | Susceptible | 1-4 | Susceptible | 4-16 | Susceptible |
| Cefepime | 27 | 24 | Susceptible | 21-24 | Susceptible | 14-18 | Susceptible |
| Imipenem | ≤0.5 | 0.5-1 | Susceptible | 2-8 | Susceptible | 4-16 | Susceptible |
| Aztreonam | 28 | 21-27 | Susceptible | 24-27 | Susceptible | 17-21 | Susceptible |
| Tobramycin | ≤1 | 2-4 | Susceptible | 2-4 | Susceptible | 4-16 | Susceptible |
| Gentamicin | ≤1 | 2-4 | Susceptible | 2-4 | Susceptible | 4-16 | Susceptible |
| Amikacin | ≤2 | 8-16 | Susceptible | 8-16 | Susceptible | 16-64 | Susceptible |
| Netilmicin | ≤1 | 2-4 | Susceptible | 2-4 | Susceptible | 8-32 | Susceptible |
| Minocycline | 20 | 17-19 | Susceptible | — | — | 12-16 | Susceptible |
| Colistin | 15 | 15 | Susceptible | 17 | Resistant | nd | nd |
| Trimethoprim-Sulphamet. | ≤20 | 2-4 | Susceptible | 2-4 | Susceptible | 2-4 | Susceptible |
| Nalidixic acid | ≤2 | 8-16 | Susceptible | NA | — | 16-32 | Susceptible |
| Norfloxacin | ≤0.5 | 0.5-1 | Susceptible | 0.5-1 | Susceptible | 4-16 | Susceptible |
| Ofloxacin | ≤0.25 | 0.5-1 | Susceptible | 0.5-1 | Susceptible | 2-8 | Susceptible |
| Ciprofloxacin | ≤0.25 | 0.5-1 | Susceptible | — | — | 1-4 | Susceptible |
| Rifampicin | 16 | 14-19 | Intermediate | — | — | nd | nd |
| Fosfomycin | 24 | 14 | Susceptible | — | — | 12-16 | Susceptible |
| Nitrofurantoin | ≤16 | 64 | Susceptible | 64 | Susceptible | 32-128 | Susceptible |

*Cc: Critical concentration

Expert finding July 2006: Penicillinase acquired

The fluctuations relative to the type of associated resistance for certain strains between Tables A1 and A2 are due to the development of the French (CA-SFM), European (EUCAST) and American (CLSI) recommendations for the categorization of bacterial strains.

5.2 EcR2: Cephalosporinase-Hyperproducing *Escherichia coli* Having an Associated Resistance to the Aminoglycosides, Quinolones and the Trimethoprim-Sulphamethoxazole Combination The bacterial and antibiogram identification is carried out by the VITEK 1 system (bioMérieux) and by the disk diffusion technique

TABLE B1

| Antibiotics | Diameter | Dmin Dmax | Results | MIC mg/L |
|---|---|---|---|---|
| Amoxicillin | | | Resistant | ≥32 |
| Amox + clavulanic acid | | | Resistant | ≥32 |
| Ticarcillin | | | Intermediate | 32 |
| C1G | | | Resistant | ≥64 |
| Cefoxitin | 11 | 15-22 | Resistant | |
| Cefotaxime | 24 | 15-21 | Intermediate | |
| Ceftazidime | 20 | 15-21 | Intermediate | |
| Imipenem | | | Susceptible | ≤4 |
| Tobramycin | 10 | 16-18 | Resistant | |
| Gentamicin | 12 | 16-18 | Resistant | |
| Netilmicin | 21 | 19-21 | Susceptible | ≤1 |
| Trimethoprim-Sulphamet. | | | Intermediate | 160 |
| Nalidixic acid | | | Resistant | ≥32 |
| Pefloxacin | | | Resistant | ≥8 |
| Nitrofurantoin | | | Susceptible | ≤25 |

The fluctuations relative to the type of associated resistance for certain strains between Tables B1 and B2 are due to the development of the French (CA-SFM), European (EUCAST) and American (CLSI) recommendations for the categorization of bacterial strains.

5.3 EcR3: ESBL-Producing *Escherichia coli* with Associated Resistance to the Aminoglycosides, Rifampicin and the Trimethoprim-Sulphamethoxazole Combination The bacterial and antibiogram identification is carried out by the VITEK 2 system (bioMérieux) and by the disk diffusion technique

TABLE C1

| Antibiotics | Diameter | Dmin Dmax | Results |
|---|---|---|---|
| Amoxicillin | 6 | 14-21 | Resistant |
| Amox + clavulanic acid | 16 | 14-21 | Intermediate |
| Ticarcillin | 6 | 18-22 | Resistant |
| Piperacillin | 13 | 12-20 | Intermediate |
| Piper + tazobactam | | | Intermediate |
| C1G | 6 | 12-18 | Resistant |
| Cefoxitin | | | Intermediate |
| Cefotaxime | 19 | 15-21 | Intermediate |
| Imipenem | 27 | 17-22 | Susceptible |
| Tobramycin | 6 | 14-16 | Resistant |
| Gentamicin | 12 | 14-16 | Resistant |
| Amikacin | 17 | 15-17 | Susceptible |
| Netilmicin | 10 | 17-19 | Resistant |
| Minocycline | 21 | 17-19 | Susceptible |
| Colistin | 16 | 15 | Susceptible |
| Trimethoprim-Sulphamet. | 6 | 10-16 | Resistant |
| Pefloxacin | 23 | 16-22 | Susceptible |
| Ciprofloxacin | 25 | 19-22 | Susceptible |
| Rifampicin | 15 | 14-19 | Intermediate |
| Fosfomycin | 23 | 14 | Susceptible |
| Cefepime | 24 | 15-21 | Intermediate |

TABLE B2

| Antibiotics | MIC mg/L (diameter in mm) | Cc*CA-SFM 2011 mg/L | CA-SFM Interpretation | Cc EUCAST 2011 | EUCAST Interpretation | Cc CLSI 2011 | CLSI Interpretation |
|---|---|---|---|---|---|---|---|
| Amoxicillin | ≥32 | 4-8 | Resistant | 8 | Resistant | 8-32 | Resistant |
| Amox + clavulanic acid | ≥32 | 4-8 | Resistant | 8 | Resistant | 8-32 | Resistant |
| Ticarcillin | 32 | 8-16 | Resistant | 8-16 | Resistant | 16-128 | Resistant |
| Cefalotine | ≥64 | 8-32 | Resistant | 16 | Resistant | 8-32 | Resistant |
| Cefoxitin | 11 | 15-22 | Resistant | 19 | Resistant | 14-18 | Resistant |
| **Cefotaxime | 24 | 23-26 | Intermediate | 18-21 | Resistant | 22-26 | Intermediate |
| **Ceftazidime | 20 | 23-26 | Resistant | 19-22 | Intermediate | 17-21 | Intermediate |
| Imipenem | ≤0.5 | 0.5-1 | Susceptible | 2-8 | Susceptible | 4-16 | Susceptible |
| Tobramycin | 10 | 16-18 | Resistant | 13-16 | Resistant | 12-15 | Resistant |
| **Gentamicin | 12 | 16-18 | Resistant | 14-17 | Resistant | 12-15 | Resistant |
| Netilmicin | ≤1 | 2-4 | Susceptible | 2-4 | Susceptible | 8-32 | Susceptible |
| Trimethoprim-Sulphamet. | 160 | 2-4 | Resistant | 2-4 | Resistant | 8-16 | Resistant |
| Nalidixic acid | ≥32 | 8-16 | Resistant | — | — | 16-32 | Resistant |
| Pefloxacin | ≥8 | 1-4 | Resistant | — | — | — | — |
| Nitrofurantoin | ≤25 | 64 | Susceptible | 64 | Susceptible | 32-128 | Susceptible |

*Cc: Critical concentration
**Note: the disk load differs between CA-SFM and EUCAST; the EUCAST interpretation is therefore not applicable in the present case. Furthermore, the technique for carrying out the disk diffusion test differs in the two reference standards.

TABLE C2

| Antibiotics | Cd* diameter in mm | CA-SFM 2011 | CA-SFM Interpretation | Cd EUCAST 2011 | EUCAST Interpretation | Cd CLSI 2011 | CLSI Interpretation |
|---|---|---|---|---|---|---|---|
| Amoxicillin | 6 | 16-19 | Resistant | 14 | Resistant | 13-17 | Resistant |
| Amox + clavulanic acid | 16 | 16-21 | Intermediate | 17 | Resistant | 13-18 | Intermediate |
| Ticarcillin | 6 | 22-24 | Resistant | 22-23 | Resistant | 14-20 | Resistant |
| Piperacillin | 13 | 16-20 | Resistant | 15-18 | Resistant | 17-21 | Resistant |
| **Piper + tazobactam | 18 | 17-21 | Intermediate | 15-18 | Susceptible | 17-21 | Intermediate |
| Cefalotine | 6 | 12-18 | Resistant | — | — | 14-18 | Resistant |
| Cefoxitin | 6 | 15-22 | Resistant | 19 | Resistant | 14-18 | Resistant |
| **Cefotaxime | 19 | 23-26 | Resistant | 18-21 | Intermediate | 22-26 | Resistant |
| Cefepime | 24 | 24 | Susceptible | 21-24 | Susceptible | 14-18 | Susceptible |
| Imipenem | 27 | 17-24 | Susceptible | 15-21 | Susceptible | 13-16 | Susceptible |
| Tobramycin | 6 | 16-18 | Resistant | 13-16 | Resistant | 12-15 | Resistant |
| **Gentamicin | 12 | 16-18 | Resistant | 14-17 | Resistant | 12-15 | Intermediate |
| Amikacin | 17 | 15-17 | Susceptible | 13-16 | Susceptible | 14-17 | Susceptible |
| **Netilmicin | 10 | 19-21 | Resistant | 12-15 | Resistant | 12-15 | Resistant |
| Minocycline | 21 | 17-19 | Susceptible | — | — | 12-16 | Susceptible |
| Colistin | 16 | 15 | Susceptible | — | — | — | — |
| Trimethoprim-Sulphamet. | 6 | 13-16 | Resistant | 13-16 | Resistant | 10-16 | Resistant |
| Pefloxacin | 23 | 16-22 | Susceptible | — | — | — | — |
| Ciprofloxacin | 25 | 22-25 | Susceptible | — | — | 15-21 | Susceptible |
| Rifampicin | 15 | 14-19 | Intermediate | — | — | — | — |
| Fosfomycin | 23 | 14 | Susceptible | — | — | 12-16 | Susceptible |

*Cd: Critical diameter
**Note: the disk load differs between CA-SFM and EUCAST; the EUCAST interpretation is therefore not applicable in the present case. Furthermore, the technique for carrying out the disk diffusion test differs in the two reference standards.

The fluctuations relative to the type of associated resistance for certain strains between Tables C1 and C2 are due to the development of the French (CA-SFM), European (EUCAST) and American (CLSI) recommendations for the categorization of bacterial strains.

5.4 SaR1: Meticillin-Resistant *Staphylococcus aureus* without Associated Resistance The bacterial and antibiogram identification is carried out by the VITEK 2 system (bioMérieux)

TABLE D1

| Antibiotics | Diameter | Dmin Dmax | Results | MIC mg/L | Results |
|---|---|---|---|---|---|
| Penicillin G | 28 | 9-29 | Resistant | ≥0.5 | Resistant |
| Oxacillin | | | | ≥8 | Resistant |
| Kanamycin | 20 | 15-17 | Susceptible | ≤4 | Susceptible |
| Tobramycin | 22 | 14-16 | Susceptible | ≤1 | Susceptible |
| Gentamicin | 23 | 14-16 | Susceptible | ≤0.5 | Susceptible |
| Chloramphenicol | 25 | 19-23 | Susceptible | | |
| Minocycline | 27 | 17-19 | Susceptible | | |
| Erythromycin | 25 | 17-22 | Susceptible | ≤0.25 | Susceptible |
| Lincomycin | 24 | 17-21 | Susceptible | ≤1 | Susceptible |
| Pristinamycin | 25 | 19-22 | Susceptible | ≤0.5 | Susceptible |
| Quinupristin-dalfopristin | | | | ≤0.25 | Susceptible |
| Trimethoprim-Sulphamet. | 26 | 10-16 | Susceptible | ≤10 | Susceptible |
| Ofloxacin | 24 | 16-22 | Susceptible | 1 | Susceptible |
| Fusidic acid | 28 | 15-22 | Susceptible | ≤0.5 | Susceptible |
| Vancomycin | | | Susceptible | ≤1 | Susceptible |
| Teicoplanin | | | Susceptible | ≤0.5 | Susceptible |
| Rifampicin | 30 | 14-29 | Susceptible | ≤0.5 | Susceptible |
| Fosfomycin | 40 | 14 | Susceptible | ≤8 | Susceptible |
| Linezolid | 29 | 24-28 | Susceptible | 2 | Susceptible |
| Minocycline | | | | ≤0.5 | Susceptible |
| Nitrofurantoin | | | | ≤16 | Susceptible |

TABLE D2

| Antibiotics | MIC mg/L | Cc*CA-SFM 2011 mg/L | CA-SFM Interpretation | Cc EUCAST 2011 | EUCAST Interpretation | Cc CLSI 2011 | CLSI Interpretation |
|---|---|---|---|---|---|---|---|
| Penicillin G | ≥0.5 | 0.12 | Resistant | 0.125 | Resistant | 0.12-0.25 | Resistant |
| Oxacillin | ≥8 | 2 | Resistant | 2 | Resistant | 2-4 | Resistant |
| Kanamycin | ≤4 | 8-16 | Susceptible | 8-16 | Susceptible | 16-64 | Susceptible |

TABLE D2-continued

| Antibiotics | MIC mg/L | Cc*CA-SFM 2011 mg/L | CA-SFM Interpretation | Cc EUCAST 2011 | EUCAST Interpretation | Cc CLSI 2011 | CLSI Interpretation |
|---|---|---|---|---|---|---|---|
| Tobramycin | ≤1 | 1 | Susceptible | 1 | Susceptible | 4-16 | Susceptible |
| Gentamicin | ≤0.5 | 1 | Susceptible | 1 | Susceptible | 4-16 | Susceptible |
| Erythromycin | ≤0.25 | 1-2 | Susceptible | 1-2 | Susceptible | 0.5-8 | Susceptible |
| Lincomycin | ≤1 | 2-8 | Susceptible | — | — | — | — |
| Pristinamycin | ≤0.5 | 1-2 | Susceptible | — | — | — | — |
| Quinupristin-dalfopristin | ≤0.25 | 1-2 | Susceptible | 1-2 | Susceptible | 1-4 | Susceptible |
| Trimethoprim-Sulphamet. | ≤10 | 2-4 | Susceptible | 2-4 | Susceptible | 2-4 | Susceptible |
| Ofloxacin | 1 | 1 | Susceptible | 1 | Susceptible | 1-4 | Susceptible |
| Fusidic acid | ≤0.5 | 1 | Susceptible | 1 | Susceptible | — | — |
| Vancomycin | ≤1 | 2 | Susceptible | 2 | Susceptible | 4-32 | Susceptible |
| Teicoplanin | ≤0.5 | 4 | Susceptible | 2 | Susceptible | 8-32 | Susceptible |
| Rifampicin | ≤0.5 | 0.06-0.5 | Susceptible | 0.064-0.5 | Susceptible | 1-4 | Susceptible |
| Fosfomycin | ≤8 | 32 | Susceptible | 32 | Susceptible | — | — |
| Linezolid | 2 | 4 | Susceptible | 4 | Susceptible | 4-8 | Susceptible |
| Minocycline | ≤0.5 | 0.5-1 | Susceptible | 0.5-1 | Susceptible | 4-16 | Susceptible |
| Nitrofurantoin | ≤16 | 64 | Susceptible | 64 | Susceptible | 32-128 | Susceptible |

*Cc: Critical concentration

February 2006: Detection of the gene mecA by the PCR technique: POSITIVE
Expert finding July 2006: totally typical phenotype: modification of the PLPs
The fluctuations relative to the type of associated resistance for certain strains between Tables D1 and D2 are due to the development of the French (CA-SFM), European (EUCAST) and American (CLSI) recommendations for the categorization of bacterial strains.

5.5 SaR3: Meticillin-Resistant *Staphylococcus aureus* Having an Associated Resistance to the Aminoglycosides and Fluoroquinolones
The bacterial and antibiogram identification is carried out by the VITEK 2 system (bioMérieux) and by the disk diffusion technique

TABLE E1

| Antibiotics | Diameter | Dmin Dmax | Results |
|---|---|---|---|
| Penicillin G | 26 | 9-29 | Resistant |
| Oxacillin | | | |
| Kanamycin | 6 | 15-17 | Resistant |
| Tobramycin | 6 | 14-16 | Resistant |
| Gentamicin | 20 | 14-16 | Susceptible |
| Chloramphenicol | 6 | 19-23 | Resistant |
| Minocycline | 26 | 17-19 | Susceptible |
| Erythromycin | 25 | 17-22 | Susceptible |
| Lincomycin | 23 | 17-21 | Susceptible |
| Pristinamycin | 23 | 19-22 | Susceptible |
| Trimethoprim-Sulphamet. | 27 | 10-16 | Susceptible |
| Ofloxacin | 6 | 16-22 | Resistant |
| Fusidic acid | 29 | 15-22 | Susceptible |
| Vancomycin | | | Susceptible |
| Teicoplanin | | | Susceptible |
| Rifampicin | 31 | 14-29 | Susceptible |
| Fosfomycin | 26 | 14 | Susceptible |
| Linezolid | 26 | 24-28 | Susceptible |

TABLE E2

| Antibiotics | diameter in mm | Cd* CA-SFM 2011 | CA-SFM Interpretation | Cd EUCAST 2011 | EUCAST Interpretation | Cd CLSI 2011 | CLSI Interpretation |
|---|---|---|---|---|---|---|---|
| Penicillin G | 26 | | Resistant | 26 | Resistant | 28-29 | Resistant |
| Cefoxitin | 17 | 25-37 | Resistant | 22 | Resistant | 21-22 | Resistant |
| **Kanamycin | 6 | 15-17 | Resistant | 16-18 | Resistant | 13-18 | Resistant |
| Tobramycin | 6 | 20 | Resistant | 18 | Resistant | 12-15 | Resistant |
| **Gentamicin | 20 | 20 | Susceptible | 18 | Susceptible | 12-15 | Susceptible |
| Erythromycin | 25 | 19-22 | Susceptible | 18-21 | Susceptible | 13-23 | Susceptible |
| Lincomycin | 23 | 17-21 | Susceptible | — | — | — | — |
| Pristinamycin | 23 | 19-22 | Susceptible | — | — | — | — |
| Trimethoprim-Sulphamet. | 27 | 13-16 | Susceptible | 14-17 | Susceptible | 10-16 | Susceptible |
| Ofloxacin | 6 | 22 | Resistant | 20 | Resistant | 14-18 | Resistant |
| Fusidic acid | 29 | 24 | Susceptible | 24 | Susceptible | — | — |
| Vancomycin | 28 | 17 | Susceptible | — | — | — | — |
| Teicoplanin | 27 | 17 | Susceptible | — | — | 10-14 | Susceptible |
| Rifampicin | 31 | 24-29 | Susceptible | 23-26 | Susceptible | 16-20 | Susceptible |
| Fosfomycin | 26 | 14 | Susceptible | — | — | — | — |

TABLE E2-continued

| Antibiotics | diameter in mm | Cd* CA-SFM 2011 | CA-SFM Interpretation | Cd EUCAST 2011 | EUCAST Interpretation | Cd CLSI 2011 | CLSI Interpretation |
|---|---|---|---|---|---|---|---|
| **Linezolid | 26 | 24 | Susceptible | 19 | Susceptible | 20-21 | Susceptible |
| Minocycline | 26 | 21-23 | Susceptible | 20-23 | Susceptible | 14-19 | Susceptible |

*Cd: Critical diameter
**Note: the disk load differs between CA-SFM and EUCAST; the EUCAST interpretation is therefore not applicable in the present case. Furthermore, the technique for carrying out the disk diffusion test differs in the two reference standards.

The fluctuations relative to the type of associated resistance for certain strains between Tables E1 and E2 are due to the development of the French (CA-SFM), European (EUCAST) and American (CLSI) recommendations for the categorization of bacterial strains.

5.6 SaR4: Meticillin-Resistant *Staphylococcus aureus* Having an Associated Resistance to the Aminoglycosides, Fluoroquinolones, Macrolides-Lincosamines-Synergistins and Ofloxacin The bacterial and antibiogram identification is carried out by the VITEK 2 system (bioMérieux) and by the disk diffusion technique

TABLE F1

| Antibiotics | Diameter | Dmin Dmax | Results | MIC mg/L |
|---|---|---|---|---|
| Penicillin G | | | Resistant | |
| Oxacillin | | | Resistant | ≥8 |
| Kanamycin | 7 | 15-17 | Resistant | |

TABLE F1-continued

| Antibiotics | Diameter | Dmin Dmax | Results | MIC mg/L |
|---|---|---|---|---|
| Tobramycin | 6 | 20-20 | Resistant | |
| Gentamicin | 21 | 20-20 | Susceptible | |
| Chloramphenicol | | | Susceptible | 8 |
| Tetracycline | | | Susceptible | ≤1 |
| Minocycline | | | Susceptible | ≤4 |
| Erythromycin | | | Resistant | ≥8 |
| Lincomycin | | | Resistant | ≥16 |
| Pristinamycin | | | Susceptible | ≤2 |
| Trimethoprim-Sulphamet. | | | Susceptible | ≤10 |
| Ofloxacin | | | Resistant | ≥8 |
| Nitrofurantoin | | | Susceptible | ≤25 |
| Fusidic acid | | | Susceptible | ≤1 |
| Vancomycin | | | Susceptible | 1 |
| Teicoplanin | | | Susceptible | ≤4 |
| Rifampicin | | | Susceptible | ≤1 |
| Fosfomycin | | | Resistant | ≥64 |

TABLE F2

| Antibiotics | MIC mg/L (diameter in mm) | Cc*CA-SFM 2011 mg/L | CA-SFM Interpretation | Cc EUCAST 2011 | EUCAST Interpretation | Cc CLSI 2011 | CLSI Interpretation |
|---|---|---|---|---|---|---|---|
| Penicillin G | | | Resistant | | Resistant | 0.12-0.25 | Resistant |
| Oxacillin | ≥8 | 2 | Resistant | 2 | Resistant | 2-4 | Resistant |
| **Kanamycin | 7 | 15-17 | Resistant | 16-18 | Resistant | 13-18 | Resistant |
| Tobramycin | 6 | 20 | Resistant | 18 | Resistant | 12-15 | Resistant |
| **Gentamicin | 21 | 20 | Susceptible | 18 | Susceptible | 12-15 | Susceptible |
| Tetracycline | ≤1 | 1-2 | Susceptible | 1-2 | Susceptible | 4-16 | Susceptible |
| Minocycline | ≤0.5 | 0.5-1 | Susceptible | 0.5-1 | Susceptible | 4-16 | Susceptible |
| Erythromycin | ≥8 | 1-2 | Resistant | 1-2 | Resistant | 0.5-8 | Resistant |
| Lincomycin | ≥16 | 2-8 | Resistant | — | — | — | — |
| Pristinamycin | ≤2 | 1-2 | Susceptible | — | — | — | — |
| Trimethoprim-Sulphamet. | ≤10 | 2-4 | Susceptible | 2-4 | Susceptible | 2-4 | Susceptible |
| Ofloxacin | ≥8 | 1 | Resistant | 1 | Resistant | 1-4 | Resistant |
| Nitrofurantoin | ≤25 | 64 | Susceptible | 64 | Susceptible | 32-128 | Susceptible |
| Fusidic acid | ≤1 | 1 | Susceptible | 1 | Susceptible | — | — |
| Vancomycin | 1 | 2 | Susceptible | 2 | Susceptible | 4-32 | Susceptible |
| Teicoplanin | ≤4 | 4 | Susceptible | 2 | Susceptible | 8-32 | Susceptible |
| Rifampicin | ≤1 | 0.06-0.5 | Susceptible | 0.064-0.5 | Susceptible | 1-4 | Susceptible |
| Fosfomycin | ≥64 | 32 | Resistant | 32 | Resistant | — | — |

*Cc: Critical concentration
**Note: the disk load differs between CA-SFM and EUCAST; the EUCAST interpretation is therefore not applicable in the present case. Furthermore, the technique for carrying out the disk diffusion test differs in the two reference standards.

The fluctuations relative to the type of associated resistance for certain strains between Tables F1 and F2 are due to the development of the French (CA-SFM), European (EUCAST) and American (CLSI) recommendations for the categorization of bacterial strains.

5.7 PaR2: *Pseudomonas aeruginosa* Having an Associated Resistance to the β-Lactams, the Trimethoprim-Sulphamethoxazole Combination and Fosfomycin The bacterial and antibiogram identification is carried out by the VITEK 2 system (bioMérieux) and by the disk diffusion technique

TABLE G1

| Antibiotics | Diameter | Dmin-Dmax | Results |
|---|---|---|---|
| Ticar + clavulanic acid | 10 | 18-22 | Resistant |
| Ticarcillin | 10 | 18-22 | Resistant |
| Piperacillin | 22 | 12-18 | Susceptible |
| Piper + tazobactam | 22 | 14-19 | Susceptible |
| Ceftazidime | 23 | 15-21 | Susceptible |
| Aztreonam | 16 | 17-23 | Resistant |
| Imipenem | 27 | 17-22 | Susceptible |
| Tobramycin | 24 | 14-16 | Susceptible |
| Gentamicin | 21 | 14-16 | Susceptible |
| Amikacin | 22 | 15-17 | Susceptible |
| Netilmicin | 19 | 17-19 | Susceptible |
| Minocycline | 6 | 17-19 | Resistant |
| Colistin | 20 | 15-15 | Susceptible |
| Trimethoprim-Sulphamet. | 6 | 10-16 | Resistant |
| Pefloxacin | 8 | 16-22 | Resistant |
| Rifampicin | 25 | 19-22 | Susceptible |
| Fosfomycin | 13 | 14-19 | Resistant |
| Ciprofloxacin | 18 | 14-14 | Susceptible |
| Cefepime | 19 | 15-21 | Intermediate |

The fluctuations relative to the type of associated resistance for certain strains between Tables G1 and G2 are due to the development of the French (CA-SFM), European (EUCAST) and American (CLSI) recommendations for the categorization of bacterial strains.

5.8 PaR3: *Pseudomonas aeruginosa* Having an Associated Resistance to the β-Lactams, the Aminoglycosides (Including the Carbapenems), the Trimethoprim-Sulphamethoxazole Combination and Ciprofloxacin The bacterial and antibiogram identification is carried out by the VITEK 2 system (bioMérieux)

TABLE H1

| Antibiotics | MIC | Results |
|---|---|---|
| Ticar + clavulanic acid | ≥128 | Resistant |
| Ticarcillin | ≥128 | Resistant |
| Piperacillin | ≥128 | Resistant |
| Piper + tazobactam | ≥128 | Resistant |
| Ceftazidime | 4 | Susceptible |
| Aztreonam | 16 | Susceptible |
| Imipenem | ≥16 | Resistant |
| Meropenem | ≥16 | Resistant |
| Tobramycin | ≥16 | Resistant |
| Gentamicin | ≥16 | Resistant |
| Amikacin | 4 | Susceptible |
| Minocycline | 4 | Resistant |
| Colistin | ≤0.5 | Susceptible |
| Trimethoprim-Sulphamet. | ≥320 | Resistant |
| Pefloxacin | 4 | Intermediate |
| Ciprofloxacin | 1 | Susceptible |
| Cefepime | 16 | Intermediate |

TABLE G2

| Antibiotics | diameter in mm | Cd* CA-SFM 2011 | CA-SFM Interpretation | Cd EUCAST 2011 | EUCAST Interpretation | Cd CLSI 2011 | CLSI Interpretation |
|---|---|---|---|---|---|---|---|
| Ticar + clavulanic acid | 10 | 22 | Resistant | 17 | Resistant | 14-15 | Resistant |
| Ticarcillin | 10 | 22 | Resistant | 17 | Resistant | 14-15 | Resistant |
| **Piperacillin | 22 | 18 | Susceptible | 19 | Susceptible | 17-18 | Susceptible |
| **Piper + tazobactam | 22 | 19 | Susceptible | 19 | Susceptible | 17-18 | Susceptible |
| **Ceftazidime | 23 | 19 | Susceptible | 16 | Susceptible | 14-18 | Susceptible |
| Cefepime | 19 | 19 | Susceptible | 18 | Susceptible | 14-18 | Susceptible |
| Aztreonam | 16 | 19-27 | Resistant | 16-50 | Resistant | 15-22 | Intermediate |
| Imipenem | 27 | 17-22 | Susceptible | 17-20 | Susceptible | 13-16 | Susceptible |
| Tobramycin | 24 | 16 | Susceptible | 16 | Susceptible | 12-15 | Susceptible |
| **Gentamicin | 21 | 16 | Susceptible | 15 | Susceptible | 12-15 | Susceptible |
| Amikacin | 22 | 15-17 | Susceptible | 15-18 | Susceptible | 14-17 | Susceptible |
| **Netilmicin | 19 | 19 | Susceptible | 12 | Susceptible | 12-15 | Susceptible |
| Minocycline | 6 | — | Resistant | — | — | — | — |
| Colistin | 20 | — | Susceptible | — | — | 10-11 | Susceptible |
| Trimethoprim-Sulphamet. | 6 | — | Resistant | 16 | Resistant | — | — |
| Ciprofloxacin | 25 | 22-25 | Susceptible | 22-25 | Susceptible | 15-21 | Susceptible |
| Rifampicin | 25 | 14-19 | Susceptible | — | — | — | — |
| Fosfomycin | 13 | 14 | Resistant | — | — | — | — |

*Cd: Critical diameter
**Note: the disk load differs between CA-SFM and EUCAST; the EUCAST interpretation is therefore not applicable in the present case. Furthermore, the technique for carrying out the disk diffusion test differs in the two reference standards.

TABLE H2

| Antibiotics | MIC mg/L | Cc*CA-SFM 2011 mg/L | CA-SFM Interpretation | Cc EUCAST 2011 | EUCAST Interpretation | Cc CLSI 2011 | CLSI Interpretation |
|---|---|---|---|---|---|---|---|
| Ticar + clavulanic acid | ≥128 | 16 | Resistant | 16 | Resistant | 64-128 | Resistant |
| Ticarcillin | ≥128 | 16 | Resistant | 16 | Resistant | 64-128 | Resistant |
| Piperacillin | ≥128 | 16 | Resistant | 16 | Resistant | 64-128 | Resistant |
| Piper + tazobactam | ≥128 | 16 | Resistant | 16 | Resistant | 64-128 | Resistant |
| Ceftazidime | 4 | 8 | Susceptible | 8 | Susceptible | 8-32 | Susceptible |
| Cefepime | 16 | 8 | Resistant | 8 | Resistant | 8-32 | Intermediate |
| Aztreonam | 16 | 1-16 | Resistant | 1-16 | Resistant | 8-32 | Intermediate |
| Imipenem | ≥16 | 4-8 | Resistant | 4-8 | Resistant | 4-16 | Resistant |
| Meropenem | ≥16 | 2-8 | Resistant | 2-8 | Resistant | 4-16 | Resistant |
| Tobramycin | ≥16 | 4 | Resistant | 4 | Resistant | 4-16 | Resistant |
| Gentamicin | ≥16 | 4 | Resistant | 4 | Resistant | 4-16 | Resistant |
| Amikacin | 4 | 8-16 | Susceptible | 8-16 | Susceptible | 16-64 | Susceptible |
| Minocycline | 4 | — | Resistant | — | — | — | — |
| Colistin | ≤0.5 | 2-4 | Susceptible | 4 | Susceptible | 2-8 | Susceptible |
| Trimethoprim-Sulphamet. | ≥320 | — | Resistant | 4 | Resistant | — | — |
| Ciprofloxacin | 1 | 0.5-1 | Intermediate | 0.5-1 | Intermediate | 1-4 | Susceptible |

*Cc: critical concentration

The fluctuations relative to the type of associated resistance for certain strains between Tables H1 and H2 are due to the development of the French (CA-SFM), European (EUCAST) and American (CLSI) recommendations for the categorization of bacterial strains.

5.9 PaR5: *Pseudomonas aeruginosa* Having an Associated Resistance to Rifampicin and the Trimethoprim-Sulphamethoxazole Combination The bacterial and antibiogram identification is carried out by the VITEK 2 system (bioMérieux) and by the disk diffusion technique

TABLE I1

| Antibiotics | Diameter | Dmin-Dmax | Results |
|---|---|---|---|
| Ticar + clavulanic acid | 40 | 18-22 | Susceptible |
| Ticarcillin | 32 | 18-22 | Susceptible |
| Piperacillin | 33 | 12-18 | Susceptible |
| Piper + tazobactam | 40 | 14-19 | Susceptible |
| Ceftazidime | 32 | 15-21 | Susceptible |
| Aztreonam | 33 | 17-23 | Susceptible |
| Imipenem | 25 | 17-22 | Susceptible |
| Meropenem | 34 | 15-20 | Susceptible |
| Tobramycin | 28 | 14-16 | Susceptible |
| Gentamicin | 25 | 14-16 | Susceptible |
| Amikacin | 27 | 15-17 | Susceptible |
| Netilmicin | 28 | 17-19 | Susceptible |
| Minocycline | 11 | 17-19 | Resistant |
| Colistin | 23 | 15 | Susceptible |
| Trimethoprim-Sulphamet. | 6 | 10-16 | Resistant |
| Norofloxacin | 17 | 22-25 | Resistant |
| Ofloxacin | 11 | 22-25 | Resistant |
| Ciprofloxacin | 30 | 19-22 | Susceptible |
| Rifampicin | 13 | 14-19 | Resistant |
| Fosfomycin | 30 | 14 | Susceptible |
| Cefepime | 32 | 15-21 | Susceptible |

TABLE I2

| Antibiotics | diameter in mm | Cd* CA-SFM 2011 | CA-SFM Interpretation | Cd EUCAST 2011 | EUCAST Interpretation | Cd CLSI 2011 | CLSI Interpretation |
|---|---|---|---|---|---|---|---|
| Ticar + clavulanic acid | 40 | 22 | Susceptible | 17 | Susceptible | 14-15 | Susceptible |
| Ticarcillin | 32 | 22 | Susceptible | 17 | Susceptible | 14-15 | Susceptible |
| **Piperacillin | 33 | 18 | Susceptible | 19 | Susceptible | 17-18 | Susceptible |
| **Piper + tazobactam | 40 | 19 | Susceptible | 19 | Susceptible | 17-18 | Susceptible |
| **Ceftazidime | 32 | 19 | Susceptible | 16 | Susceptible | 14-18 | Susceptible |
| Cefepime | 32 | 19 | Susceptible | 18 | Susceptible | 14-18 | Susceptible |
| Aztreonam | 33 | 19-27 | Susceptible | 16-50 | Intermediate | 15-22 | Susceptible |
| Imipenem | 25 | 17-22 | Susceptible | 17-20 | Susceptible | 13-16 | Susceptible |
| Meropenem | 34 | 15-22 | Susceptible | 18-24 | Susceptible | 13-16 | Susceptible |
| Tobramycin | 28 | 16 | Susceptible | 16 | Susceptible | 12-15 | Susceptible |
| **Gentamicin | 25 | 16 | Susceptible | 15 | Susceptible | 12-15 | Susceptible |
| Amikacin | 27 | 15-17 | Susceptible | 15-18 | Susceptible | 14-17 | Susceptible |
| **Netilmicin | 28 | 19 | Susceptible | 12 | Susceptible | 12-15 | Susceptible |

TABLE I2-continued

| Antibiotics | diameter in mm | Cd* CA-SFM 2011 | CA-SFM Interpretation | Cd EUCAST 2011 | EUCAST Interpretation | Cd CLSI 2011 | CLSI Interpretation |
|---|---|---|---|---|---|---|---|
| Minocycline | 11 | — | Resistant | — | — | — | — |
| Colistin | 23 | — | Susceptible | — | — | 10-11 | Susceptible |
| Trimethoprim-Sulphamet. | 6 | — | Resistant | 16 | Resistant | — | — |
| Ciprofloxacin | 30 | 22-25 | Susceptible | 22-25 | Susceptible | 15-21 | Susceptible |
| Rifampicin | 13 | 14-19 | Resistant | — | — | — | — |
| Fosfomycin | 30 | 14 | Susceptible | — | — | — | — |

*Cd: Critical diameter
**Note: the disk load differs between CA-SFM and EUCAST; the EUCAST interpretation is therefore not applicable in the present case. Furthermore, the technique for carrying out the disk diffusion test differs in the two reference standards.

The fluctuations relative to the type of associated resistance for certain strains between Tables I1 and I2 are due to the development of the French (CA-SFM), European (EUCAST) and American (CLSI) recommendations for the categorization of bacterial strains.

6. Synergism of the Combination of Cx1 with Antiseptics Against the Wild-Type Bacterial Strains

6.1 Synergism against the *E. coli* strain ATCC 25922 (wild type)

| Combinations | Initial MICs (mg/L) | Ranges tested (mg/L) | FIC index | Optimum MICs (mg/L) | Difference Cx1 MIC | Difference ATS MIC | Finding |
|---|---|---|---|---|---|---|---|
| Cx1/Hexamidine | 4/8 | 64/32 | >1 | nd | nd | nd | Indifference |
| Cx1/Chlorhexidine | 4/<1 | 64/4 | >1 | nd | nd | nd | Indifference |

6.2 Synergism against the *S. aureus* strain ATCC 29213 (wild type)

| Combinations | Initial MICs (mg/L) | Ranges tested (mg/L) | FIC index | Optimum MICs (mg/L) | Difference Cx1 MIC | Difference ATS MIC | Finding |
|---|---|---|---|---|---|---|---|
| Cx1/Hexamidine | 8/<1 | 64/4 | >1 | nd | nd | nd | Indifference |
| Cx1/Chlorhexidine | 8/<1 | 64/4 | >1 | nd | nd | nd | Indifference |

6.3. Synergism against the *P. aeruginosa* strain ATCC 27853 (wild type)

| Combinations | Initial MICs (mg/L) | Ranges tested (mg/L) | FIC index | Optimum MICs (mg/L) | Difference Cx1 MIC | Difference ATS MIC | Finding |
|---|---|---|---|---|---|---|---|
| Cx1/Hexamidine | 32/32 | 64/256 | 3 | nd | nd | nd | Indifference |
| Cx1/Chlorhexidine | 32/4 | 64/32 | 1.5 | nd | nd | nd | Indifference |

The invention claimed is:

1. A method of treating an infection by a bacterial strain having an acquired resistance to at least one defined antibiotic, comprising administering to a patient in need thereof an effective amount of a product, said patient undergoing simultaneous or sequential treatment by said antibiotic, the product comprising a calixarene represented by Formula I below:

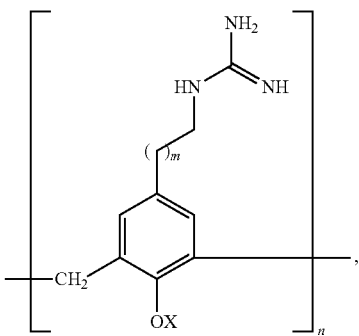

Formula I in which:
(i) n=an integer from 4 to 16,
(ii) m=an integer from 1 to 10,
(iii) X is chosen from:
a hydrogen,
an alkyl group, the number of carbons being from 1 to 20,
a halogen chosen from Cl, Br, I, or
an amphiphilic group chosen from an anionic group or a cationic group.

2. The method according to claim 1, wherein said bacterial strain has an acquired resistance to said antibiotic.

3. The method according to claim 1, wherein said bacterial strain is susceptible to said antibiotic.

4. The method according to claim 1, wherein said bacterial strain has a natural resistance to said antibiotic.

5. A method of treating an infection by a bacterial strain having a natural resistance to at least one defined antibiotic, comprising administering to a patient in need thereof an effective amount of a product, said patient undergoing simultaneous or sequential treatment with said antibiotic, the product comprising a calixarene represented by Formula I below:

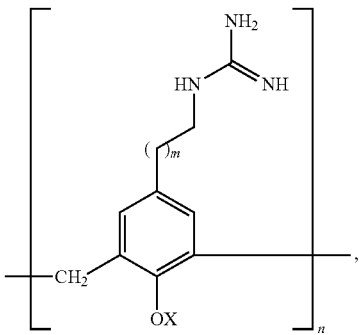

Formula I in which:
(i) n=an integer from 4 to 16,
(ii) m=an integer from 1 to 10,
(iii) X is chosen from:
a hydrogen,
an alkyl group, the number of carbons being from 1 to 20, in particular from 1 to 10,
a halogen chosen from Cl, Br, I, or
an amphiphilic group chosen from an anionic group or a cationic group.

6. The method according to claim 5, wherein said patient is undergoing simultaneous or sequential treatment with a given antibiotic to which said bacterial strain has a natural resistance.

7. The method according to claim 5, wherein said patient is undergoing simultaneous or sequential treatment with a given antibiotic to which said bacterial strain is susceptible.

8. The method according to claim 5, wherein said patient is undergoing simultaneous or sequential treatment with a given antibiotic to which said bacterial strain has an acquired resistance.

9. A method of treating infection by at least one bacterial strain having a resistance to at least one defined antibiotic, on patients undergoing simultaneous or sequential treatment with a given antibiotic to which said bacterial strain optionally has a resistance, or pathologies involving a wild-type bacterial strain having no acquired resistance to any known antibiotic, on patients undergoing simultaneous or sequential treatment with a "given antibiotic" to which said bacterial strain has no resistance, comprising administering to a patient in need thereof an effective amount of a product comprising a calixarene represented by Formula I below:

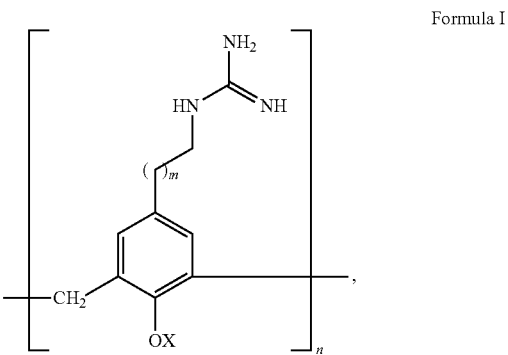

Formula I in which:
(i) n=an integer from 4 to 16,
(ii) m=an integer from 1 to 10,
(iii) X is chosen from:
a hydrogen,
an alkyl group, the number of carbons being from 1 to 20,
a halogen chosen from Cl, Br, I, or
an amphiphilic group chosen from an anionic group or a cationic group.

10. The method according claim 9, wherein the pathologies involve a resistant bacterial strain belonging to a species chosen from *Escherichia coli, Pseudomonas aeruginosa*, and *Staphylococcus aureus.*

11. The method according claim 10, wherein the pathologies involve a resistant bacterial strain chosen from:
a wild-type strain of *Staphylococcus aureus,*
a strain of meticillin-resistant *Staphylococcus aureus* (MRSA) without associated resistance,
a strain of MRSA having a resistance to the aminoglycosides and fluoroquinolones,
a strain of MRSA having a resistance to the aminoglycosides, fluoroquinolones, macrolides-lincosamides-synergystins and ofloxacin,
a wild-type strain of *Escherichia coli,* an ESBL (extended spectrum β-Lactamase)-producing strain of *Escherichia coli*, having an associated resistance to the aminoglycosides, rifampicin and the trimethoprime-sulphamethoxazole combination, a penicillinase-producing, strain of *Escherichia coli* without associated resistance, a cephalosporinase-hyperproducing having an associated resistance to the aminoglycosides, quinolones and the trimethoprime-sulphamethoxazole combination, a wild-type strain of *Pseudomonas aeruginosa*, a strain of *Pseudomonas aeruginosa* having a resistance to the β-lactams, the trimethoprime-sulphamethoxazole combination and fosfomycin, a strain of *Pseudomonas aeruginosa* having a resistance to the β-lactams (including the carbapenems), aminoglycosides, the trimethoprime-sulphamethoxazole combination and ciprofloxacin, a mucoid strain of *Pseudomonas aeruginosa* having a resistance to rifampicin and the trimethoprime-sulphamethoxazole combination.

12. The method according to claim 9, wherein said given antibiotic is chosen from the group constituted by the β-lactams, aminoglycosides, fluoroquinolones, fosfomycin, colimycin, rifampicin, tigecycline, or fusidic acid.

13. The method according to claim 12, wherein said given antibiotic is chosen from imipenem, piperacillin-tazobactam, penicillin G, cefotaxime, ceftazidime, tobramycin, gentamicin, ciprofloxacin, rifampicin fosfomycin, colimycin, tigecycline, ticarcillin-clavulanic acid, streptomycin or fusidic acid.

\* \* \* \* \*